United States Patent [19]

Effland et al.

[11] Patent Number: 4,794,181

[45] Date of Patent: Dec. 27, 1988

[54] 1-ARYLOXY-2,3,4,5-TETRAHYDRO-3-BEN-ZAZEPINES

[75] Inventors: Richard C. Effland; Joseph T. Klein, both of Bridgewater; Larry Davis, Sergeantsville, all of N.J.

[73] Assignee: Hoechst-Roussel Pharmaceuticals, Inc., Somerville, N.J.

[21] Appl. No.: 819,439

[22] Filed: Jan. 16, 1986

Related U.S. Application Data

[63] Continuation of Ser. No. 541,767, Oct. 13, 1983, abandoned, which is a continuation-in-part of Ser. No. 387,916, Jun. 14, 1982.

[51] Int. Cl.$^4$ .................................. C07D 223/16
[52] U.S. Cl. ..................................... 540/594
[58] Field of Search ............................. 540/594, 595

[56] References Cited

U.S. PATENT DOCUMENTS 3,388,130 6/1968 Pesson .................................. 546/141
3,393,192 7/1968 Walter et al. ......................... 540/595

OTHER PUBLICATIONS

Likforman et al, C.R. Acad. Sc. Paris 1268 pp. 2340 & 2341 (1969).

*Primary Examiner*—Glennon H. Hollrah
*Assistant Examiner*—D. B. Springer
*Attorney, Agent, or Firm*—Jerome Rosenstock; Tatsuya Ikeda

[57] ABSTRACT

The invention relates to 1-aryloxy-2,3,4,5-tetrahydro-3-benzazepines of the formula

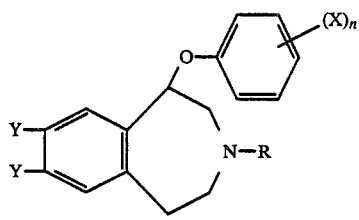

wherein Y is the same of different and is hydrogen and lower alkoxy; X is hydrogen, halogen, lower alkyl, lower alkoxy, $CF_3$, $NO_2$, CN and $NH_2$; R is hydrogen, lower alkyl, cycloalkyllower alkyl,

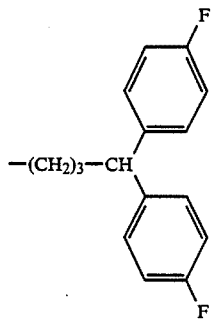

Ar lower alkyl of the formula

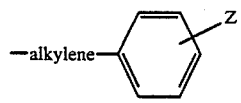

where Z is hydrogen, lower alkyl, lower alkoxy, halogen $CF_3$, $NO_2$ and $NH_2$; Aryloxy lower alkyl of the formula

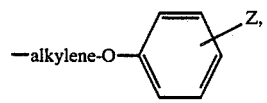

where Z is as previously defined; and an alkylene amine of the formula

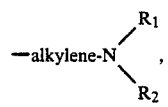

where $R_1$ and $R_2$ are the same or different and are hydrogen and lower alkyl, n is an integer of 1 or 2; and the pharmaceutically acceptable acid addition salts thereof.

22 Claims, No Drawings

1-ARYLOXY-2,3,4,5-TETRAHYDRO-3-BENZAZE-PINES

This is a continuation, of application Ser. No. 541,767 filed Oct. 13, 1983, abandoned, which is a continuation-in-part application of application Ser. No. 387,916, filed June 14, 1982.

To the best of our knowledge the compounds of the present invention have not heretofore been described or suggested.

The compounds of the present invention have the general formula

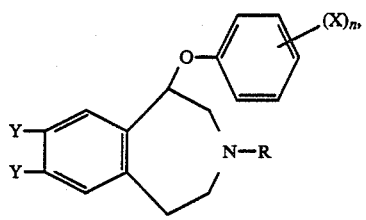

where Y is the same or different and is hydrogen and lower alkoxy; X is hydrogen, halogen, lower alkyl, lower alkoxy, $CF_3$, CN, $NO_2$ and $NH_2$; R is hydrogen, lower alkyl, cycloalkyl lower alkyl

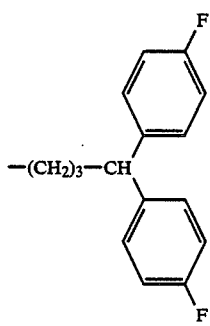

Ar lower alkyl of the formula

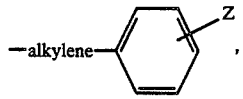

where Z is hydrogen, halogen, lower alkyl, lower alkoxy, $CF_3$, $NO_2$ and $NH_2$; Aryloxy lower alkyl of the formula

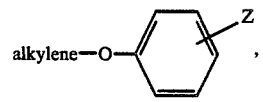

where Z is as previously defined, and alkylene amine of the formula

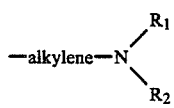

where $R_1$ and $R_2$ are the same or different and are hydrogen and lower alkyl; n is an integer of 1 or 2; and the pharmaceutically acceptable acid addition salts thereof.

In the above definitions the term "lower" means the group it is describing contains from 1 to 6 carbon atoms. The term "alkyl" refers to a straight or branched chain hydrocarbon containing no unsaturation, e.g. methyl, ethyl, isopropyl, 2-butyl, neopentyl, n-hexyl, etc.; the term "alkoxy" refers to a monovalent substituent which consists of an alkyl group linked through an ether oxygen having its free valence bond from the ether oxygen, e.g. methoxy, ethoxy, propoxy, butoxy, pentoxy, etc., the term "cycloalkyl lower alkyl" refers to a monovalent substituent consisting of a saturated hydrocarbon group possessing at least one carbocyclic ring, of 3 to 7 carbon atoms, e.g. cyclopropyl, cyclobutyl, cyclopentyl, cyclohexyl, cycloheptyl, etc. linked through a lower alkyl group havings its free valence bond from a carbon of the lower alkyl group; the term "Ar lower alkyl" refers to a monovalent substituent which consists of an aryl group, e.g., phenyl, p-nitrophenyl, o-toluyl, m-methoxy phenyl, etc. linked through a lower alkylene group having its free valence bond from a carbon of the lower alkylene group, and having a formula of

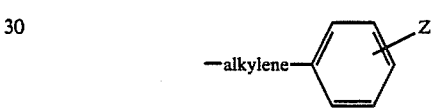

where the Z is hydrogen, halogen, lower alkyl, lower alkoxy, $CF_3$, $NO_2$ and $NH_2$; the term "alkylene" refers to a bivalent radical of the lower branched or unbranched alkyl group it is derived from having valence bonds from two terminal carbons thereof, e.g. ethylene ($-CH_2CH_2-$), propylene ($-CH_2CH_2CH_2-$)isopropylene $$(CH_3-\overset{|}{C}H-CH_2-),$$

etc.; the term "Aryloxy lower alkyl" refers to a monovalent substituent which consists of an aryl group, as defined above, linked through an ether oxygen linked through a lower alkylene group, as defined above, having its free valence bond from a carbon of the lower alkylene group, and having a formula of

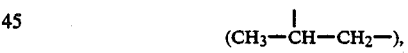

where Z is as defined above; and the term "halogen" refers to a member of the family consisting of fluorine, chlorine, bromine and iodine.

The compounds of the present invention are prepared in the following manner. The substituents Y, X, R, $R_1$ and $R_2$ are as defined above unless indicated otherwise. A substituted benzazepine of the formula

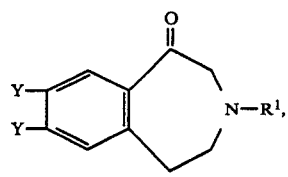

where R[1] is the tosyl group

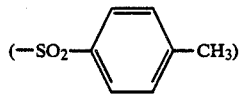

or the mesyl group (—SO$_2$CH$_3$), is selected. Compound I is reduced in a conventional manner, by reaction with NaBH$_4$, to form a substituted 1-hydroxy-2,3,4,5-tetrahydro-3-benzazepine of the formula

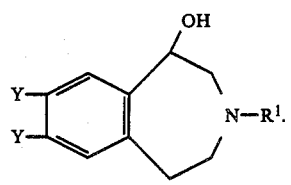

Compound II is detosylated or demesylated by means of reduction with a metal such as Na°or K°, in liquid ammonia or ethanol, or by reduction with sodium bis(2-methoxyethoxy) aluminum hydride etc., to form a 1-hydroxy-2,3,4,5-tetrahydro-3-benzazepine of the formula

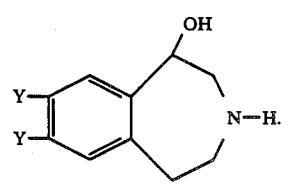

The preparation of compound I, its reduction to compound II and the detosylation or demesylation of compound II to yield compound III are well known and are easily arrived at by one skilled in the art from the prior art such as M. A. Rehman, et al., *J. Chem. Soc.* (C) 58 (1967) and G. Hazebroucq, *Ann. Chim.*, I, 221 to 254 (1966), both of which are incorporated by reference hereinto.

Compound III is reacted with a halide having the formula

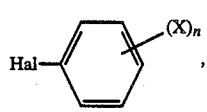

where X is as previously defined, and Hal is a halogen selected from F, Cl, Br and I to form a compound of the invention

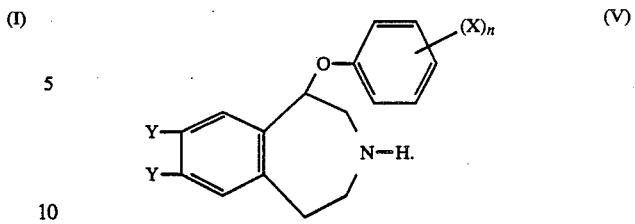

Compound V is typically obtained by reacting compounds III and IV under nucleophilic reaction conditions, such as those of the conventional Williamson ether synthesis, as for example in the presence of a strong base, e.g. NaH, and an inert solvent, e.g. dimethylformamide (DMF), dimethylsulfoxide (DMSO), benzene, toluene, and temperature of 0° to 120° C. for 2 to 96 hours.

Compound V can also be prepared in the following manner. Compound II is reacted with halide IV in the manner described above to form an intermediate of the invention hving the formula

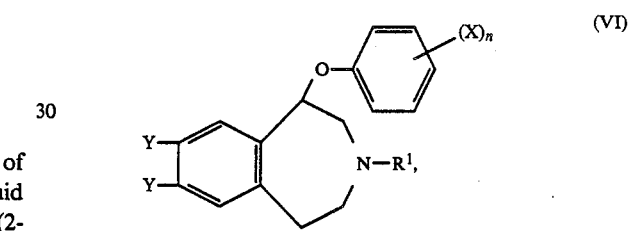

where R[1] is tosyl or mesyl. Compound VI is then reacted under conventional conditions with the well-known reducing agent sodium bis(2-methoxyethoxy)aluminum hydride, NaAlH$_2$(OCH$_2$CH$_2$OCH$_3$)$_2$, e.g. in an inert solvent, such as toluene, at a temperature of 25° to 70° C. for 24 to 48 hours, to detosylate or demesylate compound VI to form compound V. In an alternative manner, compound II is reacted with a phenol of the formula

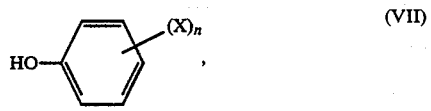

in the manner described in U.S. Pat. No. 4,216,218. That is, compound II and compound VII are combined with triphenylphosphine and a solvent, e.g., benzene. Diethylazodicarboxylate is then added to the resultant solution. The resultant reaction mixture is maintained under a nitrogen atmosphere at a temperature of 5° to 25° C., typically for 6 to 30 hours to form intermediate compound VI which in turn is then reacted with the sodium bis(2-methoxyethoxy)aluminum hydride to form compound V of the invention.

Compound V of the invention is reacted under conventional nucleophilic reaction conditions with a halide VIIA having the formula Hal-R$_3$, (VIIA), where Hal is a halogen selected from F, Cl, Br and I and R$_3$ is selected from lower alkyl; cycloalkyl lower alkyl;

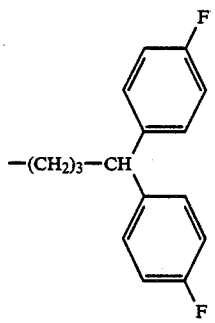

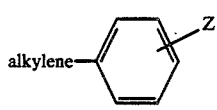

where the alkylene moiety is of 1 to 6 carbon atoms and Z is selected from hydrogen, halogen, lower alkyl, lower alkoxy, $CF_3$, $NO_2$ and $NH_2$; Aryloxy lower alkyl of the formula

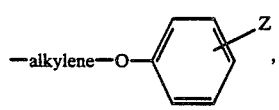

where Z is as previously defined,

where $R_4$ is alkyl of 1 to 5 carbon atoms or

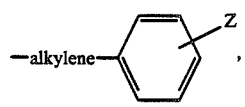

where the alkylene moiety is of 1 to 5 carbon atoms and Z is as defined above; -alkylene-CN, where the alkylene moiety is of 1 to 5 carbon atoms;

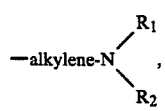

where the alkylene moiety is of 1 to 6 carbon atoms; and

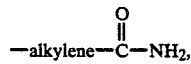

where the alkylene moiety is of 1 to 5 carbon atoms, to form a compound of the invention

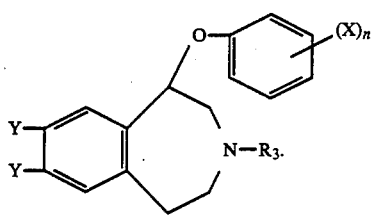

Typically, compound V is reacted with halide VIIA in the presence of a base, e.g., $NaHCO_3$, $K_2CO_3$, $Na_2CO_3$, etc. and an inert solvent, e.g. DMF, butanol, acetone, 2-butanone, etc., at a temperature of 70° to 120° C. for 2 to 24 hours, to form compound VIII. Where $R_3$ is lower alkyl or Ar lower alkyl of the formula

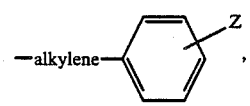

or Aryloxy lower alkyl of the formula

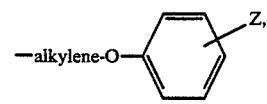

typically this reaction is carried out in the presence of $K_2CO_3$ or $Na_2CO_3$, at a temperature of 70° to 120° C. for 2 to 24 hours to form compound VIII where $R_3$ is lower alkyl or

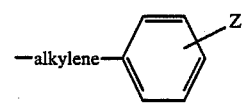

(Aryloxy lower alkyl) or

-alkylene-O-⟨Ar⟩-Z (Aryloxy lower alkyl).

When $R_3$ of halide VIIA is $$-\overset{O}{\underset{\|}{C}}-R_4,$$

typically the reaction is run in the presence of a base such as $NaHCO_3$, triethylamine, etc., a solvent such as $CH_2Cl_2$, $CHCl_3$, etc. at a temperature ranging from 5° to 60° C. for 2 to 24 hours to produce a compound VIII where $R_3$ is

which is an intermediate of the invention having the formula

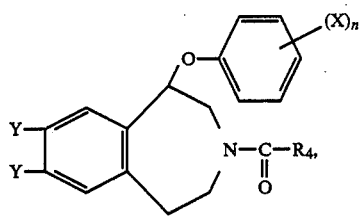 (IX)

where R₄ is as previously defined. The carbonyl group of compound IX is reduced to a methylene group in a conventional manner with such reducing agents as metal hydrides, e.g., LiAlH₄, sodium bis(2-methoxyethoxy)aluminum hydride, etc., to form a compound of VIII of the invention where $R_3$ is lower alkyl or Ar lower alkyl having the formula

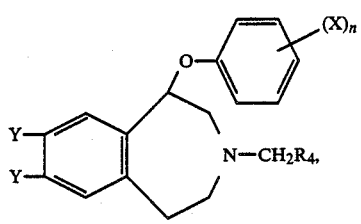 (X)

where R4 is as defined above.

In an alternative procedure to produce compound VIII where $R_3$ is methyl, compound V is reacted in a conventional manner with a lower alkyl haloformate, e.g. ethylchloroformate, to form an intermediate of the invention

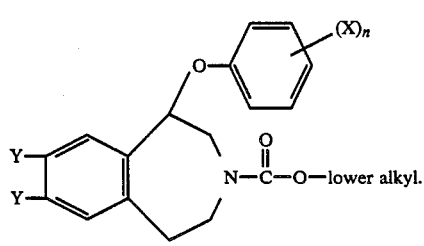 (XI)

Compound XI can then be reduced in a conventional manner, such as by treatment with LiAlH₄, etc. to form compound VIII where $R_3$ is methyl,

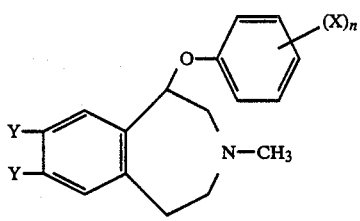 (XII)

Where halide VIIA is a halo substituted alkyl nitrile, e.g. chloroacetonitrile, the halide VIIA is reacted with compound V in the presence of a base, e.g. NaHCO₃, K₂CO₃, etc., in a suitable solvent, e.g. DMF etc., at a temperature of 25° to 60° C. for 1 to 3 hours to form compound VIII where $R_3$ is -alkylene-CN, that is an intermediate compound of the invention having the formula

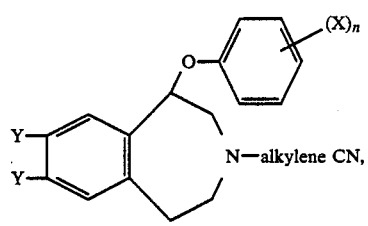 (XIV)

where the alkylene moiety is of 1 to 5 carbon atoms.

Compound XIV in turn is reduced by conventional means, e.g. with a metal hydride such as LiAlH₄, sodium bis-(2-methoxyethoxy)-aluminum hydride or borane, etc. in an inert solvent such as THF etc., at a temperature of 25° to 65° C. for 1 to 3 hours to reduce the cyano group to form a compound of the invention

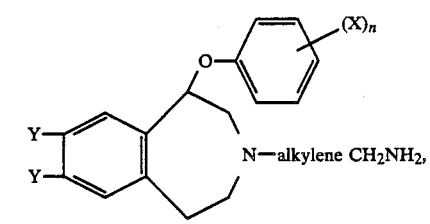

where the alkylene moiety is of 1 to 5 carbon atoms, (XV).

Where halide VIIA is a halo substituted alkylamine(N-substituted or unsubstituted), halide VIIA and compound V are typically reacted in the presence of a base, e.g. Na₂CO₃, K₂CO₃, etc. and a solvent, e.g. DMF, n-butanol, etc. at a temperature of 25° to 80° C. for 1 to 3 hours to form compound VIII of the invention where $R_3$ is

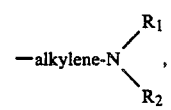

where the alkylene moiety is of 1 to 6 carbon atoms,

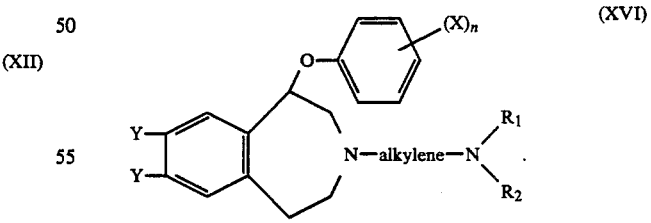 (XVI)

In an alternative embodiment, compound V is reacted with a branched or straight chained alkenyl cyanide having a formula Alkenyl-CN where the alkenyl moiety is 1 to 5 carbon atoms, e.g. acrylonitrile, typically at a temperature of 25° to 80° C. for 1 to 20 hours to form the intermediate compound of the invention whereby there is addition across the unsaturated bond to form the intermediate compound of the invention having the formula

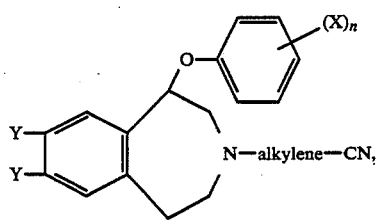

where the alkylene moiety has 1 to 5 carbon atoms, (XIV).

The intermediate XIV is reduced, as described above, to form the compound of the invention having the formula

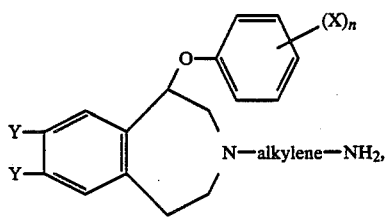

where the alkylene moiety has 2 to 6 carbon atoms (XV).

The N-alkyl derivatives of compounds XV and compound XVI where $R_1$ and/or $R_2$ is hydrogen, are prepared in a conventional manner, as for example by reaction with an alkyl halide compound whereby a mono- or di-substituted compound is obtained, where at least $R_1$ or $R_2$ is lower alkyl. Alternatively these compounds can be reacted with an alkyl or aryl chloroformate followed by reduction of the resultant compound, as with LiAlH$_4$$_L$, or sodium bis(2-methoxyethoxy)aluminum hydride, to form a compound of the invention where at least $R_1$ or $R_2$ is methyl.

It is understood that when X and/or Z is nitro that such group can be reduced to amino using conventional reducing agents and conditions, e.g. treatment with a metal and acid; catalytically with hydrogen and Pt, Pd, etc.; or a metal hydride, such as LiAlH$_4$.

The utility of the compounds of the present invention in the treatment of depression in mammals is demonstrated by their ability to inhibit tetrabenazine induced ptosis in mice [International Journal of Neuropharmacology 8, 73 (1969)], a standard assay for useful antidepressant properties. The antidepressant activities of some of the compounds of the invention expressed in terms of a 50% inhibition of ptosis of tetrabenazine-induced ptosis in mice is given in Table I.

TABLE I

| Compound | ED$_{50}$ (oral) (mg/kg of body weight) |
|---|---|
| 7,8-dimethoxy-3-methyl-1-phenoxy-2,3,4,5-tetrahydro-3-benzazepine oxalate | 3.8 |
| 7,8-dimethoxy-1-phenoxy-2,3,4,5-tetrahydro-3-benzazepine oxalate | 3.7 |
| 3-(2-aminoethyl)-1-(3-chlorophenoxy)-2,3,4,5-tetrahydro-3-benzazepine dioxalate | 7.5 • |
| 1-(3-chlorophenoxy)-7,8- | 4.2 |

TABLE I-continued

| Compound | ED$_{50}$ (oral) (mg/kg of body weight) |
|---|---|
| dimethoxy-2,3,4,5-tetrahydro-3-benzazepine oxalate | |
| desipramine | 2.3 |

The utility of the compounds of the present invention in the treatment of depression in mammals is further demonstrated by their ability to potentiate the effects of 5-hydroxytryptophan in rats [Neuropharmacology 16, 663 (1977)], an assay for compounds interacting with the serotonergic system, indicative of antidepressant potential. The antidepressant activities of some of the compounds of the invention expressed in terms of a potentiation of 5-hydroxytryptophan induced seizures in 50% of the animals is given in Table II.

TABLE II

| Compound | ED$_{50}$ (intraperitoneal) (mg/kg of body weight) |
|---|---|
| 1-(3-chlorophenoxy-7,8-dimethoxy-2,3,4,5-tetrahydro-3-benzazepine oxalate | 1.1 |
| 7,8-dimethoxy-1-phenoxy-2,3,4,5-tetrahydro-3-benzazepine oxalate | 0.85 |
| 7,8-dimethoxy-3-methyl-1-phenoxy-2,3,4,5-tetrahydro-3-benzazepine oxalate | 7.5 |
| 7,8-dimethoxy-1-(4-fluorophenoxy)-2,3,4,5-tetrahydro-3-benzazepine maleate | 2.9 |
| 7,8-dimethoxy-1-phenoxy-3-(n-propyl)-2,3,4,5-tetrahydro-3-benzazepine oxalate | 0.7 |
| 7,8-dimethoxy-1-(4-methoxyphenoxy)-2,3,4,5-tetrahydro-3-benzazepine maleate | 0.9 |
| 7,8-dimethoxy-3-methyl-1-(4-methylphenoxy)-2,3,4,5-tetrahydro-3-benzazepine maleate | 0.9 |
| 1-(4-trifluoromethylphenoxy)-2,3,4,5-tetrahydro-3-benzazepine oxalate | 2.9 |

These data indicate that the compound of the present invention would be useful as antidepressants in mammals when administered in amounts ranging from 0.1 to 50 mg/kg of body weight per day.

The compounds of the invention are also useful as antihy0pertensive agents due to their ability to depress blood pressure in mammals. Antihypertensive activity is measured in the spontaneous hypertensive rat by the indirect tail cuff method described in "Methods in Pharmacology", A. Schwartz, Ed., Vol. I, Appleton-Century Crofts, New York, 1971, p. 135. In this procedure a group of five animals are treated orally for three days with the test compound in relation to the control group of the same number. The drop in blood pressure is measured on the third day following administration. The antihypertensive activities of some of the compounds, expressed as mm decrease in mean arterial blood pressure are given in Table III.

TABLE III

| Compound | Dose mg/kg of body weight | Decrease in Blood Pressure mm HG |
|---|---|---|
| 3-methyl-1-(4-methyl-phenoxy-2,3,4,5-tetrahydro-3-benzazepine hydrobromide | 50 | 35 |
| 1-(4-methoxyphenoxy)-3- | 50 | 48 |

TABLE III-continued

| Compound | Dose mg/kg of body weight | Decrease in Blood Pressure mm HG |
|---|---|---|
| methyl-2,3,4,5-tetrahydro-3-benzazepine hydrobromide | | |
| 3-(2-amino-1-methyl)ethyl-2,3,4,5-tetrahydro-1-(4-trifluoromethylphenoxy)-3-benzazepine dioxalate | 50 | 51 |
| 3-(2-methylaminoethyl)-2,3,4,5-tetrahydro-1-(4-trifluoromethylphenoxy)-3-benzazepine dioxalate | 50 | 33 |
| 7,8-dimethoxy-3-methyl-2,3,4,5-tetrahydro-1-(4-trifluoromethylphenoxy)-3-benzazepine hydrochloride | 50 | 43 |
| 7,8-dimethoxy-2,3,4,5-tetrahydro-1-(4-trifluoromethylphenoxy)-3-benzazepine oxalate | 50 | 49 |
| 3-(2-aminoethyl)-2,3,4,5-tetrahydro-1-(4-trifluoromethylphenoxy)-3-benzazepine dioxalate | 50 | 61 |
| guanethidine | 50 | 20 |

Blood pressure reduction is achieved when the compounds of the invention are administered to a subject requiring such treatment at an effective oral, parenteral or intravenous dose of from 0.1 to 50 mg/kg of body weight per day. A preferred effective dose with this range is from about 0.1 to 5 mg/kg of body weight per day. A particularly preferred effective amount is about 1 mg/kg of body weight per day. It is to be understood, however, that for any particular subject, specific dosage regimens should be adjusted according to the individual need and the professional judgment of the person administering or supervising the administration of the compounds of the invention. It is to be further understood that the dosages set forth herein are examples only and that they do not, to any extent, limit the scope or practice of the invention.

The compounds of the invention are also useful as analgesic agents due to their ability to alleviate pain in mammals. The activity of the compound is demonstrated in the 2-phenyl-1,4-benzoquinone-induced writhing test in mice, a standard assay for analgesia [Proc. Soc. Exptl. Biol. Med., 95, 729 (1957)]. The analgesic activity of some of the compounds expressed in terms of percent inhibition of writhing are given in Table IV.

TABLE IV

| Compound | Dose (subcutaneous) mg/kg of Body Weight) | Inhibition of Writhing % |
|---|---|---|
| 7,8-dimethoxy-1-(4-methoxyphenoxy)-3-methyl-2,3,4,5-tetrahydro-3-benzazepine hydrochloride | 7.6 | 50 |
| 7,8-dimethoxy-3-methyl-1-phenoxy-2,3,4,5-tetrahydro-3-benzazepine oxalate | 20 | 58 |
| 1-(4-methoxyphenoxy)-3-methyl-2,3,4,5-tetrahydro-3-benzazepine hydrobromide | 20 | 46 |
| 3-(3-aminopropyl)-2,3,4,5-tetrahydro-1-(4-trifluoromethylphenoxy)-3-benzazepine dimaleate | 8.2 | 50 |
| 1-(3-chlorophenoxy)-3-(2-phenylethyl)-2,3,4,5-tetrahydro-3-benzazepine oxalate | 25 | 42 |
| 1-(3-chlorophenoxy)-3-cyclopropylmethyl-2,3,4,5-tetrahydro-3-benzazepine oxalate | 25 | 66 |
| 7,8-dimethoxy-3-methyl-2,3,4,5-tetrahydro-1-(4-trifluoromethylphenoxy)-3-benzazepine hydrochloride | 5.7 | 50 |
| propoxyphene | 3.9 | 50 |

The analgesic relief of pain is achieved when the compounds of the invention are administered to a subject requiring such treatment at an effective oral, parenteral or intravenous dose of from 0.1 to 25 mg/kg of body weight per day. A preferred effective dose within this range is from about 1 to 10 mg/kg of body weight per day. A particularly preferred effective amount is about 2 mg/kg of body weight per day. It is to be understood, however, that for any particular subject, specific dosage regimens should be adjusted according to the individual need. It is further to be understood that the dosages set forth herein are examples only and that they do not, to any extent limit the scope or practice of the invention.

The compounds of the present invention may be administered to a subject as a composition comprising the compound and an inert compound, e.g. an inert adjuvant, which is conventional in pharmaceutical preparations or compositions.

Effective amounts of the compounds of the present invention may be administered to a subject by one of various methods, for example, orally as in capsules or tablets, parenterally in the form of sterile solutions or suspensions, and in some cases intravenously in the form of sterile solutions. The compounds of the invention, while effective themselves, may be formulated and administered in the form of their pharmaceutically acceptable acid addition salts for purposes of stability, convenience of crystallization, increased solubility and the like.

Preferred pharmaceutically acceptable acid addition salts include those derived from inorganic acids such as hydrochloric, hydrobromic, sulfuric, nitric, phosphoric, perchloric acids and the like as well as organic acids such as tartaric, citric, acetic, succinic, maleic, fumaric acids and the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the 1-aryloxy-2,3,5-tetrahydro-3-benzazepine of the invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage unit form contains between 5.0–300 milligrams of the 1-aryloxy-2,3,4,5-tetrahydro-3-benzazepines of the invention.

The tablets, pills, capsules, troches and the like may also contain the following adjuvants: a binder such as microcrystalline cellulose, gum tragacanth or gelatin; and excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of the 1-aryloxy-2,3,4,5-tetrahydro-3-benzazepines of the invention, but may be varied to be between 0.1 and about 50% of the weight thereof. The amount of the invention compound present in such compositions is such that a suitable dosage will be obtained. Preferred compositions and preparations according to the present invention are prepared so that a parenteral dosage unit contains between 5.0 to 100 milligrams of the 1-aryloxy-2,3,4,5-tetrahydro-3-benzazepines of the invention.

The solutions or suspensions may also include the following adjuvants: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Other compounds of the invention include:
7,8-dimethoxy-1-(4-fluorophenoxy)-2,3,4,5-tetrahydro-3-benzazepine;
7,8-dimethoxy-1-(4-fluorophenoxy)-3-methyl-2,3,4,5-tetrahydro-3-benzazepine;
1-(4-chlorophenoxy)-7,8-dimethoxy-2,3,4,5-tetrahydro-3-benzazepine;
1-(4-chlorophenoxy)-7,8-dimethoxy-3-methyl-2,3,4,5-tetrahydro-3-benzazepine;
1-(3,4-dichlorophenoxy)-7,8-dimethoxy-2,3,4,5-tetrahydro-3-benzazepine;
1-(3,4-dichlorophenoxy)-7,8-dimethoxy-3-methyl-2,3,4,5-tetrahydro-3-benzazepine;
1-(4-bromophenoxy)-7,8-dimethoxy-2,3,4,5-tetrahydro-3-benzazepine;
1-(4-bromophenoxy)-7,8-dimethoxy-3-methyl-2,3,4,5-tetrahydro-3-benzazepine;
7,8-dimethoxy-1-(2-fluorophenoxy)-2,3,4,5-tetrahydro-3-benzazepine;
7,8-dimethoxy-1-(2-fluorophenoxy)-3-methyl-2,3,4,5-tetrahydro-3-benzazepine;
1-(2-chlorophenoxy)-7,8-dimethoxy-2,3,4,5-tetrahydro-3-benzazepine;
1-(2-chlorophenoxy)-7,8-dimethoxy-3-methyl-2,3,4,5-tetrahydro-3-benzazepine;
7,8-dimethoxy-1-phenoxy-3-(n-propyl)-2,3,4,5-tetrahydro-3-benzazepine; and
7,8-dimethoxy-3-ethyl-1-phenoxy-2,3,4,5-tetrahydro-3-benzazepine.

The following examples are for illustrative purposes and are not to be construed as limiting the invention disclosed herein. All temperatures are given in degrees centigrade unless indicated otherwise.

EXAMPLE 1

1-(p-Trifluoromethylphenoxy)-2,3,4,5-tetrahydro-3-benzazepine oxalate

A solution of 1-hydroxy-2,3,4,5-tetrahydro-3-benzazepine (9.78 g; 0.06 mole) in dimethylformamide (DMF) [150 ml] was added at room temperature to a suspension of sodium hydride (3.1 g. 50% (98%) oil dispersion, 0.063 mole, washed twice with hexane) in DMF (75 ml). The mixture was stirred at room temperature for one hour, and a solution of p-fluorobenzotrifluoride (10.35 g, 0.063 mole) in DMF (60 ml) was added. This mixture was stirred at room temperature about 16 hours overnight. The reaction was warmed at 70° C. for one hour then stirred at room temperature overnight again. The mixture was poured into an ice/water mixture and extracted with dichloromethane; the dichloromethane extract was washed four times with water then once with saturated sodium chloride, then treated with charcoal, filtered through Celite-MgSO$_4$, and dried over MgSO$_4$. Removal of the solvent yielded 14 g of an oil (76%). A solution of oxalic acid in ether was added to a solution of 4 g. of the oil in ether to give 3 g of product. Recrystallization from ethyl acetate-methanol yielded 2 g of 1-(p-trifluoromethylphenoxy)-2,3,4,5-tetrahydro-3-benzazepine oxalate m.p. 208°–209° C.

ANALYSIS: Calculated for $C_{17}H_{16}F_3NO.(CO_2H)_2$: 57.42%C, 4.57%H, 3.52%N, Found: 57.32%C, 4.40%H, 3.34%N.

EXAMPLE 2

1-(p-Chlorophenoxy)-2,3,4,5-tetrahydro-3-benzazepine oxalate

A solution of 1-hydroxy-2,3,4,5-tetrahydro-3-benzazepine (14.3 g, 0.088 mole) in DMF (190 ml) was added at room temperature to a suspension of sodium hydride (4.9 g. 50% (98%) oil dispersion, 0.10 mole, washed twice with hexane) in DMF (50 ml). The mixture was stirred at room temperature for one hour, warmed to 65° C. for one hour, then cooled again to room temperature. A solution of 4-fluorochlorobenzene (13.8 g; 0.11 mole) in DMF (40 ml) was added. The mixture was stirred at room temperature overnight (about 16 hours) then was warmed at 75° C. for six hours. The solvent was removed in vacuo to yield an oil which was stirred with water, then extracted with dichloromethane. The organic extracts were washed twice with water then dried (saturated NaCl, anhydrous MgSO$_4$). The solution was filtered and then concentrated to an oil (20 g) which was dissolved in ether then converted to the oxalate salt as in Example 1 (6 g, 19%, m.p. 80°–90° C.). This material was twice recrystallized from ethyl acetate/methanol to yield 1-(p-chlorophenoxy)-2,3,4,5-tetrahydro-3-benzazepine oxalate, d @198°–199.5° C.

ANALYSIS: Calculated for $C_{16}H_{16}ClNO.(CO_2H)_2$: 59.42%C, 4.99%H, 3.85%N, Found: 59.25%C, 5.20%H, 4.05%N.

EXAMPLE 3

1-(p-Nitrophenoxy)-2,3,4,5-tetrahydro-3-benzazepine hydrochloride

A solution of 1-hydroxy-2,3,4,5-tetrahydro-3-benzazepine (7.5 g, 0.046 mole) in DMF (90 ml) was added at room temperature to a suspension of sodium hydride (2.7 g. 50% [98%] oil dispersion, 0.055 mole, washed twice with hexane) in DMF (25 ml). The mixture was warmed to 50° C. for one hour, then cooled to 0°–5° C. then a solution of 1-fluoro-4-nitrobenzene (7.5 g. 0.053 mole) in DMF (10 ml) was added. The mixture was stirred at room temperature for four hours. The solvent was removed to yield an oil which was stirred with water, then extracted with chloroform. The organic extracts were washed twice with water then dried (saturated NaCl, anhydrous $MgSO_4$). The solution was filtered, then concentrated to an oil (14 g) which was dissolved in hot methanol/ether. The oil was then converted to the hydrochloride salt (5.5 g of a solid, 37%, d 218°–220° C.) by the addition of ethereal -HCl. This material was twice recrystallized from ethyl acetate/methanol to yield 1-(p-nitrophenoxy)-2,3,4,5-tetrahydro-3benzazepine hydrochloride, d 227°–228° C.

ANALYSIS: Calculated for $C_{16}H_{16}N_2O_3.HCl$: 59.91%C, 5.34%H, 8.74%N, Found: 59.77%C, 5.30%H, 8.37%N.

EXAMPLE 4

1-(m-Chlorophenoxy)-2,3,4,5-tetrahydro-3-benzazepine oxalate

A solution of 1-hydroxy-2,3,4,5-tetrahydro-3-benzazepine (14.0 g., 0.086 mole) in DMF (90 ml) was added at room temperature to a suspension of sodium hydride (5.0 g, 50% (98%) oil dispersion, 0.10 mole, washed twice with hexane) in DMF (25 ml). The mixture was stirred at room temperature for one hour, warmed briefly at 50° C. and cooled. A solution of 1-chloro-3-fluorobenzene (12.9 g, 0.10 mole) in DMF (15 ml) was added thereto. The resultant reaction mixture was stirred at room temperature overnight (about 16 hours) then at 70° C. for one hour. The mixture was cooled, then concentrated to an oil which was stirred with water and then extracted with dichloromethane. The organic phases were washed twice with water then dried (saturated NaCl, anhydrous $MgSO_4$). The solution was filtered then concentrated to an oil which was dissolved in ether and then converted to the oxalate salt as in Example 1 (14.5 g, 46%, d 196°–200° C.). 4.5 g of the resultant oxalate salt was twice recrystallized from ethyl acetate/methanol solution to yield 1-(m-chlorophenoxy)-2,3,4,5-tetrahydro-3-benzazepine oxalate, d 202°–202.5° C.

ANALYSIS: Calculated for $C_{16}H_{16}ClNO.(CO_2H)_2$: 59.42%C, 4.99%H, 3.85%N, Found: 59.20%C, 5.15%H, 3.84%N.

EXAMPLE 5

1-(m-Chlorophenoxy)-3-(3-N,N-dimethylaminopropyl)-2,3,4,5-tetrahydro-3-benzazepine dioxalate A mixture of 1-(m-chlorophenoxy)-2,3,4,5-tetrahydro-3-benzazepine of Example 4, (6.4 g., 0.023 mole), 3-dimethylaminopropyl chloride (5.7 g, 0.047 mole), potassium carbonate (10.0 g) and 0.01 g of potassium iodide in n-butanol (100 ml) was refluxed for three hours. The reaction mixture was cooled, then concentrated to an oil which was stirred with water and then extracted with ether and then with chloroform. The combined organic phases were washed twice with water, then dried (saturated NaCl, anhydrous $MgSO_4$). The solution was filtered, then concentrated to an oil (7.5 g) which was dissolved in ether, then converted to the dioxalate salt (7.0 g., 56%, d @ 82°–115° C.) utilizing the procedure of Example 1. This material was twice recrystallized from a 20:1 ethyl acetate/methanol solution to yield 1-(m-chlorophenoxy)-3-(3-N,N-dimethylaminopropyl)-2,3,4,5-tetrahydro-3-benzazepine dioxalate, (3.5 g, d @ 190°–190.5° C.).

ANALYSIS: Calculated for $C_{21}H_{27}ClN_2O.2C_2H_2O_4$: 55.71%C, 5.80%H, 5.20%N, Found: 55.75%C, 5.93%H, 5.18%N.

EXAMPLE 6

1-(m-Trifluoromethylphenoxy)-2,3,4,5-tetrahydro-3-benzazepine hydrobromide

A solution of 1-hydroxy-2,3,4,5-tetrahydro-3-benzazepine (8.0 g., 0.049 mole) in DMF (90 ml) was added at room temperature to a suspension of sodium hydride (2.9 g 50% oil dispersion (98%), 0.059 mole, washed twice with hexane) in DMF (25 ml). The mixture was warmed to 45° C. for one hour, cooled to room temperature, and a solution of m-fluorobenzotrifluoride (9.3 g, 0.056 mole) in DMF (20 ml) was added. The mixture was stirred at room temperature overnight. The solvent was removed in vacuo to yield an oil which was stirred with water, then extracted with dichloromethane. The organic extracts were washed twice with water, then dried (saturated NaCl, anhydrous $MgSO_4$). The solution was filtered, then concentrated to an oil (9.5 g) which was dissolved in ether, then converted to the hydrobromide salt by the addition of ethereal HBr (4.0 g., 38%, d 109°–110° C.). This material was twice recrystallized from a 25:1 ethyl acetate/methanol solution to yield 1-(m-trifluoromethylphenoxy)-2,3,4,5-tetrahydro-3-benzazepine hydrobromide, d 111° C.

ANALYSIS: Calculated for $C_{17}H_{16}F_3NO.BHr$: 52.59%C, 4.41%H, 3.61%N, Found: 52.44%C, 4.24%H, 3.39%N.

EXAMPLE 7

1-(m-Chlorophenoxy)-3-methyl-2,3,4,5-tetrahydro-3-benzazepine

To a cooled solution of 1-(m-chlorophenoxy)-2,3,4,5-tetrahydro-3-benzazepine of Example 4, (6.5 g., 0.024 mole) and triethylamine (2.8 g, 0.028 mole) in chloroform (75 ml) was slowly dropped ethyl chloroformate (3.0 g, 0.028 mole) in chloroform (10 ml.). The reaction mixture was stirred overnight, about 16 hours, at ambient temperature, then was concentrated to an oil which was dissolved in ether, washed with water, dilute HCl, again twice washed with water, then dried (saturated NaCl, anhydrous $MgSO_4$). The solution was filtered, then concentrated to an oil (7.5 g, 90%). A solution of the oil in tetrahydrofuran (THF) (75 ml) was slowly dropped into a refluxing suspension of LiAlH$_4$ (1.6 g. 0.042 mole) in THF (125 ml). After refluxing five hours, the mixture was cooled, then was quenched by dropwise addition of saturated NH$_4$Cl solution. The mixture was diluted with ether, filtered, washed twice with water then dried (saturated NaCl, anhydrous MgSO$_4$). The solution was filtered, then concentrated to an oil (5.6 g., 93%). This oil was distilled to yield an oil of 1-(m-chlorophenoxy)-3-methyl-2,3,4,5-tetrahydro-3-benzazepine (150°–170° C./0.1 mm).

ANALYSIS: Calculated for C$_{17}$H$_{18}$ClNO: 70.95%C, 6.30%H, 4.87%N, Found: 71.23%C, 6.40%H, 4.69%N.

EXAMPLE 8

3-(3-N,N-Dimethylaminopropyl)-2,3,4,5-tetrahydro-1-(p-trifluoromethylphenoxy)-3-benzazepine dihydrochloride A mixture of 2,3,4,5-tetrahydro-1-(p-trifluoromethylphenoxy)-3-benzazepine of Example 1, (6.2 g, 0.020 mole), 3-dimethylaminopropyl chloride (4.9 g. 0.040 mole), potassium carbonate (10 g) and potassium iodide in n-butanol (100 ml) was refluxed three hours. The mixture was cooled, filtered, then concentrated to an oil which was stirred with water then extracted with ether and then with chloroform. The organic extracts were washed twice with water, then dried (saturated NaCl, anhydrous MgSO$_4$). The solution was filtered then concentrated to an oil (5.8 g) which was dissolved in ether and then converted to the dihydrochloride salt (hygroscopic) by the addition of ethereal-HCl. This material was immediately recrystallized from a 25:1 solution of ethyl acetate/methanol to yield 3-(3-N,N-dimethylaminopropyl)-2,3,4,5-tetrahydro-1-(p-trifluoromethylphenoxy)-3-benzazepine dihydrochloride, (3.0 g, 32%, d 235°–236° C.).

ANALYSIS: Calculated for C$_{22}$H$_{27}$F$_3$N$_2$O.2HCl: 56.78%C, 6.28%H, 6.02%N, Found: 56.43%C, 6.14%H, 5.75%N.

EXAMPLE 9 a.

3-Phenylacetyl-2,3,4,5-tetrahydro-1-(p-trifluoromethylphenoxy)-3-benzazepine To a cooled solution of 2,3,4,5-tetrahydro-1-(p-trifluoromethylphenoxy)-3-benzazepine of Example 1 (5.8 g. 0.019 mole) and triethylamine (2.3 g, 0.023 mole) in chloroform (75 ml) was slowly dropped phenylacetyl chloride (3.5 g. 0.023 mole) in chloroform (10 ml). After stirring at ambient temperature overnight the reaction mixture was concentrated to an oil. The oil was dissolved in ether, then washed with water, dilute HCl (10%), again with water and dried (saturated NaCl, anhydrous MgSO$_4$). The solution was filtered, concentrated to an oil which was extracted with boiling hexanes and then concentrated to an oil (6.8 g, 84%). A sample was distilled to yield an oil of 3-phenylacetyl-2,3,4,5-tetrahydro-1-(p-trifluoromethylphenoxy)-3-benzazepine, 240°–250° C./0.1 mm.

ANALYSIS: Calculated for C$_{25}$H$_{22}$F$_3$NO$_2$: 70.57%C, 5.21%H, 3.29%N, Found: 70.28%C, 5.19%H, 2.98%N.

b.

3-(2-Phenylethyl)-2,3,4,5-tetrahydro-1-(p-trifluoromethylphenoxy)-3-benzazepine A solution of 3-phenylacetyl-2,3,4,5-tetrahydro-1-(p-trifluoromethylphenoxy)-3-benzazepine of Example 9a. (6.5 g, 0.015 mole) in THF (100 ml) was slowly dropped into a refluxing suspension of LiAlH$_4$ (1.2 g, 0.030 mole) in THF (75 ml). After refluxing four hours the mixture was cooled, then quenched by dropwise addition of saturated NH$_4$Cl. The mixture was diluted with ether, filtered, washed twice with water and dried (saturated NaCl, anhydrous MgSO$_4$). The solution was filtered, then concentrated to an oil (6.2 g., 92%). This oil was distilled to yield an oil of 3-(2-phenylethyl)-2,3,4,5-tetrahydro-1-(p-trifluoromethylphenoxy)-3-benzazepine, 220°–235° C./0.1 mm.

ANALYSIS: Calculated for C$_{25}$H$_{24}$F$_3$NO: 72.97%C, 5.88%H, 3.41%N, Found: 72.72%C, 5.65%H, 3.33%N.

EXAMPLE 10

1-(m-Chlorophenoxy)-3-(2-phenylethyl)-2,3,4,5-tetrahydro-3-benzazepine oxalate A solution of phenylacetyl chloride (4.3 g, 0.028 mole) in chloroform (10 ml) was slowly dropped into a cooled solution of 1-(m-chlorophenoxy)-2,3,4,5-tetrahydro-3-benzazepine of Example 4 (6.5 g, 0.024 mole) and triethylamine (2.8 g. 0.028 mole) in chloroform (75 ml).

After stirring at ambient temperature overnight, the reaction mixture was concentrated to an oil which was dissolved in ether, then washed with water, dilute HCl (10%), twice with water and dried (saturated NaCl, anhydrous MgSO$_4$). The solution was filtered, then concentrated to an oil (9.5 g). This oil was dissolved in tetrahydrofuran (THF) [75 ml] and slowly dropped into a refluxing suspension of LiAlH$_4$ (1.6 g, 0.042 mole) in THF (125 ml). Ater refluxing five hours, the reaction mixture was cooled, then quenched by drop-wise addition of saturated NH$_4$Cl (50 ml). The mixture was diluted with ether, filtered, washed twice with water and dried (saturated NaCl, anhydrous MgSO$_4$). The solution was filtered then concentrated to an oil (8.0 g, 88%). This oil was dissolved in ether then converted to the oxalate salt to yield 1-(m-chlorophenoxy)-3-(2-phenylethyl)-2,3,4,5-tetrahydro-3-benzazepine oxalate (2.4 g, d.p. 95°–96° C.), using the procedure of Example 1.

ANALYSIS: Calculated for C$_{24}$H$_{24}$ClNO.(CO$_2$H)$_2$: 66.73%C, 5.60%H, 2.99%N, Found: 66.60%C, 5.32%H, 2.75%N.

EXAMPLE 11 a.

3-Ethoxycarbonyl-2,3,4,5-tetrahydro-1-(p-trifluoromethylphenoxy)-3-benzazepine To a cooled solution of 2,3,4,5-tetrahydro-1-(p-trifluoromethylphenoxy)-3-benzazepine of Example 1 (6.3 g, 0.021 mole) and triethylamine (2.1 g, 0.024 mole) in chloroform (70 ml) was slowly dropped a solution of ethyl chloroformate (2.6 g, 0.024 mole) in chloroform (20 ml). After stirring six hours at ambient temperature the reaction mixture was concentrated to an oil. The oil was dissolved in ether, washed with water, dilute HCl, again twice with water and then dried (saturated NaCl, anhydrous MgSO$_4$). The solution was filtered and then concentrated to yield an oil (8.0 g). A sample was distilled to yield an oil of 3-ethoxycarbonyl-2,3,4,5-tetrahydro-1-(p-trifluoromethylphenoxy)-3-benzazepine, 195° C./0.1 mm.

ANALYSIS: Calculated for $C_{20}H_{20}F_3NO_3$: 63.32%C, 5.31%H, 3.69%N, Found: 63.44%C, 5.35%H, 3.55%N.

b.
3-Methyl-2,3,4,5-tetrahydro-1-(p-trifluoromethylphenoxy)-3-benzazepine hydrochloride A solution of 3-ethoxycarbonyl-2,3,4,5-tetrahydro-1-(p-trifluoromethylphenoxy)-3-benzazepine of Example 11a (7.0 g. 0.018 mole) in THF (100 ml) was slowly dropped into a refluxing suspension of $LiAlH_4$ (1.4 g. 0.036 mole) in THF (75 ml). After refluxing four hours, the reaction mixture was cooled, then quenched by dropwise addition of saturated $NH_4Cl$. The mixture was diluted with ether, filtered, washed twice with water and dried (saturated NaCl, anhydrous $MgSO_4$). The solution was filtered, then concentrated to an oil (5.1 g), which was dissolved in ether and converted to the hydrochloride salt (5.1 g., 80%, d 203°–206° C.) by the addition of ethereal HCl. This material was twice recrystallized from ethyl acetate/methanol solution to yield 3-methyl-2,3,4,5-tetrahydro-1-(p-trifluoromethylphenoxy)-3-benzazepine hydrochloride, d 210°–211° C.

ANALYSIS: Calculated for $C_{18}H_{18}F_3NO.HCl$: 60.42%C, 5.35%H, 3.92%N, Found: 60.84%C, 5.20%H, 3.66%N.

EXAMPLE 12

1-(m-Chlorophenoxy)-3-(n-propyl)-2,3,4,5-tetrahydro-3-benzazepine

A mixture of 1-(m-chlorophenoxy)-2,3,4,5-tetrahydro-3-benzazepine of Example 4 (6.4 g, 0.023 mole), 1-bromopropane (5.7 g., 0.047 mole) and sodium bicarbonate (8.4 g, 0.10 mole) in DMF (100 ml) was stirred at 70° C. for three hours. The mixture was concentrated under high vaccum to an oil which was stirred with water then extracted with ether. The ether extracts were washed twice with water and dried (saturated NaCl, anhydrous $MgSO_4$). The solution was filtered, then concentrated to an oil (6.3 g, 86%) which was distilled to yield an oil of 1-(m-chlorophenoxy)-3-(n-propyl)-2,3,4,5-tetrahydro-3-benzazepine, 190°–210° C./0.1 mm.

ANALYSIS: Calculated for $C_{19}H_{22}ClNO$: 72.25%C, 7.02%H, 4.44%N, Found: 71.93%C, 7.02%H, 4.20%N.

EXAMPLE 13

1-(m-Chlorophenoxy)-3-cyclopropylmethyl-2,3,4,5-tetrahydro-3-benzazepine oxalate A mixture of 1-(m-chlorophenoxy)-2,3,4,5-tetrahydro-3-benzazepine of Example 4, (7.0 g. 0.026 mole), chloromethylcyclopropane (4.6 g, 0.051 mole) and sodium bicarbonate (8.4 g, 0.10 mole) in DMF (85 ml) was warmed at 80°–90° C. for four hours. The reaction mixture was cooled, then concentrated under high vacuum to an oil which was stirred with water and extracted with ether. The ether extracts were twice washed with water and dried (saturated NaCl, anhydrous $MgSO_4$). The solution was filtered, then concentrated to an oil which was dissolved in ether and then converted to the oxalate salt (7 g, mp 80°–95° C.) using the procedure of Example 1. This material was rebasified, then passed through a silica gel dry column with ethyl acetate as eluent. The desired product was extracted with ethyl acetate then concentrated to an oil (3.3 g). This oil was converted to the oxalate salt using the procedure of Example 1 and then immediately recrystallized from a 20:1 solution of ethyl acetate/methanol to yield 1-(m-chlorophenoxy)-3-cyclopropylmethyl-2,3,4,5-tetrahydro-3-benzazepine oxalate, (3.1 g, d 100°–101° C.).

ANALYSIS: Calculated for $C_{20}H_{22}ClNO.(CO_2H)_2$: 63.23%C, 5.79%H, 3.35%N, Found: 63.04%C, 5.78%H, 3.35%N.

EXAMPLE 14

3-[2-(p-Nitrophenylethyl)]-2,3,4,5-tetrahydro-1-(p-trifluoromethylphenoxy)-3-benzazepine hydrobromide A mixture of 2,3,4,5-tetrahydro-1-(p-trifluoromethylphenoxy)-3-benzazepine of Example 1 (13.0 g, 0.042 mole), p-nitrophenethyl bromide (11.7 g, 0.05] mole), sodium bicarbonate (18 g, 0.21 mole) and 0.01 g of KI in DMF (100 ml) was warmed at 90° C. for six hours. The reaction mixture was cooled, filtered and concentrated to an oil which was stirred with water then extracted with ether. The ether extracts were washed with water and dried (saturated $MgSO_4$). The solution was filtered then concentrated to an oil (20 g). The oil was passed through a silica gel dry column using ethyl acetate as the eluent. The desired product was extracted with ethyl acetate, filtered and concentrated to an oil (16 g) which was dissolved in ether, then converted to the hydrobromide salt (8 g, 35%, m.p. 98°–108°) by the addition of ethereal HBr. A 3.0 g. sample was recrystallized from a 20:1 solution of ethyl acetate/methanol to yield 3-[2-(p-nitrophenylethyl)]-2,3,4,5-tetrahydro-1-(p-trifluoromethylphenoxy)-3-benzazepine hydrobromide (2.4 g, d 216°–217° C.).

ANALYSIS: Calculated for $C_{25}H_{23}F_3N_2O_3.HBr$: 55.87%C, 4.50%H, 5.21%N, Found: 55.69%C, 4.61%H, 5.20%N.

EXAMPLE 15

3-[2-(4-Aminophenylethyl)]-2,3,4,5-tetrahydro-1-(p-trifluoromethylphenoxy)-3-benzazepine dioxalate A solution of 3-[2-(p-nitrophenylethyl)]-2,3,4,5-tetrahydro-1-(p-trifluoromethylphenoxy)-3-benzazepine hydrobromide of Example 14 (6.0 g., 0.011 mole) in glacial acetic acid (50 ml) was dropped into a stirred suspension of zinc dust (3.5 g., 0.049 mole) in 50% aqueous acetic acid (60 ml). After stirring one hour at ambient temperature, the mixture was filtered and the zinc and inorganic salts were washed with 3N HCl. The filtrate was basified with 6N NaOH and extracted with ether. The ether extracts were washed twice with water and dried (saturated NaCl, anhydrous $MgSO_4$). The solution was filtered and concentrated to an oil (4.5 g) which was dissolved in ether and converted to the dioxalate salt (5.5 g, 82%, d 120°–140° C.) using the procedure of Example 1. This material was recrystallized from a solution of ethyl acetate/methanol to yield 3-[2-(4-aminophenylethyl)]-2,3,4,5-tetrahydro-1-(p-trifluoromethylphenoxy)-3-benzazepine dioxalate, d 157°–158° C.

ANALYSIS: Calculated for $C_{25}H_{25}F_3N_2O.2(CO_2H)_2$: 57.42%C, 4.82%H, 4.62%N, Found: 57.16%C, 4.71%H, 4.62%N.

EXAMPLE 16 a.
3-Propionyl-2,3,4,5-tetrahydro-1-(p-trifluoromethylphenoxy)-3-benzazepine To a cooled solution of 2,3,4,5-tetrahydro-1-(p-trifluoromethylphenoxy)-3-benzazepine of Example 1 (6.5 g, 0.021 mole) and triethylamine (2.5 g, 0.025 mole) in chloroform (75 ml) was slowly dropped propionyl chloride (2.3 g. 0.025 mole) in chloroform (10 ml). After stirring at ambient temperature two hours the reaction mixture was concentrated to an oil which was dissolved in ether then washed with water, dilute HCl, again twice with water and dried (saturated NaCl, anhydrous MgSO$_4$). The solution was filtered then concentrated to a solid (7.2 g, 95%, m.p. 98°–105° C.). A sample was twice recrystallized from hexanes to yield 3-propionyl-2,3,4,5-tetrahydro-1-(p-trifluoromethylphenoxy)-3-benzazepine, m.p. 109°–110° C.

ANALYSIS: Calculated for $C_{20}H_{20}F_3NO_2$: 66.10%C, 5.55%H, 3.86%N, Found: 65.99%C, 5.52%H, 3.75%N.

b.
3-(n-Propyl)-2,3,4,5-tetrahydro-1-(p-trifluoromethylphenoxy)-3-benzazepine hydrobromide A solution of 3-propionyl-2,3,4,5-tetrahydro-1-(p-trifluoromethylphenoxy)-3-benzazepine of Example 16a (6.5 g, 0.018 mole) in THF (100 ml) was dropped into a refluxing suspension of LiAlH$_4$ (1.4 g, 0.036 mole) in THF (75 ml). After refluxing four hours, the reaction mixture was cooled, diluted with ether and quenched by dropwise addition of saturated NH$_4$Cl. The mixture was filtered, washed twice with water and was dried (saturated NaCl, anhydrous MgSO$_4$). The solution was filtered and concentrated to an oil (5.0 g) which was passed through a silica gel dry column using ethyl acetate as the eluent. The desired product was extracted with ethyl acetate, filtered and concentrated to an oil (5.2 g). The oil was then distilled to yield an oil (3.9 g, 62%, 180°–185° C./0.1 mm). This oil was dissolved in ether, filtered, and converted to the hydrobromide salt by the addition of ethereal HBr which was recrystallized from a 20:1 solution of ethyl acetate/methanol to yield 3-(n-propyl)-2,3,4,5-tetrahydro-1-(p-trifluoromethylphenoxy)-3-benzazepine hydrobromide, (3.5 g. 45%, d193° C.).

ANALYSIS: Calculated for $C_{20}H_{22}F_3NO.HBr$: 55.82%C, 5.39%H, 3.26%N, Found: 55.42%C, 5.24%H, 3.18%N.

EXAMPLE 17

3-Cyclopropylmethyl-2,3,4,5-tetrahydro-1-(p-trifluoromethylphenoxy)-3-benzazepine hydrobromide A mixture of 2,3,4,5-tetrahydro-1-(p-trifluoromethylphenoxy)-3-benzazepine of Example 1, (7.0 g, 0.023 mole), chloromethylcyclopropane (4.1 g, 0.046 mole), sodium bicarbonate (8.4 g, 0.10 mole) and 0.01 g of KI in DMF (85 ml) was warmed at 75°–80° C. for five hours. The reaction mixture was cooled then concentrated under high vacuum to an oil which was stirred with water and extracted with ether. The ether extracts were washed twice with water and dried (saturated NaCl, anhydrous MgSO$_4$). The solution was filtered and concentrated to an oil (7 g) which was passed through a silica gel dry column with ethyl acetate as the eluent. The desired product was extracted with ethyl acetate, filtered and concentrated to an oil (6 g) which was distilled to yield an oil (3.5 g). This oil was converted to the hydrobromide salt by the addition of ethereal HBr and immediately recrystallized from a 25:1 solution of ethyl acetate/methanol to yield 3-cyclopropylmethyl-2,3,4,5-tetrahydro-1-(p-trifluoromethylphenoxy)-3-benzazepine hydrobromide (1.4 g, 14%, d 198°–198.5° C.).

ANALYSIS: Calculated for $C_{21}H_{22}F_3NO.HBr$: 57.02%C, 5.24%H, 3.17%N, Found: 56.78%C, 5.16%H, 3.10%N.

EXAMPLE 18 a.
3-Cyanomethyl-2,3,4,5-tetrahydro-1-(p-trifluoromethylphenoxy)-3-benzazepine A mixture of 2,3,4,5-tetrahydro-1-(p-trifluoromethylphenoxy)-3-benzazepine of Example 1 (16 g, 0.052 mole), chloroacetonitrile (8 g, 0.10 mole) and sodium bicarbonate (17 g, 0.20 mole) in DMF (125 ml) was warmed at 70° C. for 2.5 hours. The mixture was concentrated to an oil which was stirred with water and extracted with ethyl acetate. The organic extracts were washed twice with water and dried (saturated NaCl, anhydrous MgSO$_4$). After filtering, the solvent was evaporated to an oil (18 g) which solidified upon triturating with petroleum ether to a solid (16.5 g, 92%, m.p. 125°–129° C.). A sample was recrystallized from hexanes to yield 3-cyanomethyl-2,3,4,5-tetrahydro-1-(p-trifluoromethylphenoxy)-3-benzazepine, m.p. 134°–135° C.

ANALYSIS: Calculated for $C_{19}H_{17}F_3N_2O$: 65.88%C, 4.95%H, 8.09%N, 16.46.F, Found: 65.56%C, 4.91%H, 7.96%N, 16.03%F.

b.
3-(2-Aminoethyl)-2,3,4,5-tetrahydro-1-(p-trifluoromethylphenoxy)-3-benzazepine dioxalate A solution of 3-cyanomethyl-2,3,4,5-tetrahydro-1-(p-trifluoromethylphenoxy)-3-benzazepine of Example 18a. (16 g, 0.046 mole) in THF (100 ml) was dropped into a suspension of LiAlH$_4$ (7.2 g, 0.19 mole) in THF (100 ml). After refluxing for twenty hours the mixture was cooled, then quenched by dropwise addition of saturated NH$_4$Cl. The mixture was diluted with ether, filtered, washed twice with water and dried (saturated NaCl, anhydrous MgSO$_4$). The solution was filtered and evaporated to an oil (14 g) of which 3 g was converted to the dioxalate salt (4.5 g, d 160°–165° C.) using the procedure of Example 1. This material was twice recrystallized from a 20:1 solution of ethyl acetate/methanol to yield 3-(2-aminoethyl-2,3,4,5-tetrahydro-1-(p-trifluoromethylphenoxy)-3-benzazepine dioxalate (2.3 g, d 173°–174° C.).

ANALYSIS: Calculated for $C_{19}H_{21}F_3N_2O.2(CO_2H)_2$: 52.07%C, 4.75%H, 5.28%N, Found: 51.67%C, 4.75%H, 5.31%N.

EXAMPLE 19

7,8-Dimethoxy-2,3,4,5-tetrahydro-1-(p-trifluoromethylphenoxy)-3-benzazepine oxalate A solution of 7,8-dimethoxy-1-hydroxy-2,3,4,5-tetrahydro-3-benzazepine (9 g, 0.040 mole) in DMF (50 ml) was added at room temperature to a suspension of sodium hydride (2.4 g. 50% oil dispersion, 0.048 mole) (washed twice with hexane) in DMF (10 ml). The mixture was stirred at 70° C. for one hour, then was cooled to 50° C. and a solution of p-fluorobenzotrifluoride (8 g, 0.048 mole) in DMF (10 ml) was added. After stirring twenty hours at ambient temperature, the mixture was concentrated to an oil which was stirred with water and extracted with ethyl acetate-ether. The combined organic phases were washed twice with water and dried (saturated NaCl, anhydrous MgSO$_4$). The solution was filtered, then concentrated to an oil which was dissolved in ether then converted to the oxalate salt (10 g, 55%, d 110° C.), using the procedure of Example 1. 3.0 g of material was twice recrystallized from a 20:1 ethyl acetate/methanol solution to yield 7,8-dimethoxy-2,3,4,5-tetrahydro-1-(p-trifluoromethylphenoxy)-3-benzazepine oxalate, d 143°–144° C.

ANALYSIS: Calculated for C$_{19}$H$_{20}$F$_3$NO$_3$.(CO$_2$H)$_2$: 55.14%C, 4.85%H, Found: 55.00%C, 5.17%H.

EXAMPLE 20 a.

7,8-Dimethoxy-3-ethoxycarbonyl-2,3,4,5-tetrahydro-1-(p-trifluoromethylphenoxy)-3-benzazepine To a cooled solution of 7,8-dimethoxy-2,3,4,5-tetrahydro-1-(p-trifluoromethylphenoxy)-3-benzazepine (5.5 g, 0.015 mole) and triethylamine (1.7 g, 0.017 mole) in chloroform (70 ml) was slowly dropped a solution of ethyl chloroformate (1.0 g, 0.017 mole) in chloroform (20 ml). After stirring twenty hours at ambient temperature the reaction mixture was concentrated to an oil which was dissolved in ether, washed with water, dilute HCl, again twice with water, then dried (saturated NaCl, anhydrous MgSO$_4$). The solution was filtered then concentrated to a solid (5.0 g, 76%, m.p. 120° C.) of which a sample was twice recrystallized from hexanes to yield 7,8-dimethoxy-3-ethoxycarbonyl-2,3,4,5-tetrahydro-1-(p-trifluoromethylphenoxy)-3-benzazepine, m.p. 130°–131° C.

ANALYSIS: Calculated for C$_{22}$H$_{24}$F$_3$NO$_5$: 60.13%C, 5.51% H, Found: 60.34%C, 5.42%H.

b.

7,8-Dimethoxy-3-methyl-2,3,4,5-tetrahydro-1-(p-trifluoromethylphenoxy)-3-benzazepine hydrochloride A solution of 7,8-dimethoxy-3-ethoxycarbonyl-2,3,4,5-tetrahydro-1-(p-trifluoromethylphenoxy)-3-benzazepine of Example 20a, (4.5 g, 0.010 mole) in THF (60 ml) was slowly dropped into a stirred suspension of LiAlH$_4$ (0.8 g, 0.020 mole) in THF (100 ml). After refluxing three hours, the reaction mixture was cooled, diluted with ether, then quenched by dropwise addition of saturated NH$_4$Cl (60 ml). The mixture was filtered and the organic layer was washed twice with water and dried (saturated NaCl, anhydrous MgSO$_4$). The solution was filtered, then concentrated to an oil which was dissolved in ether and converted to the hydrochloride salt (4.0 g, 95% d 188°–190° C.) by the addition of ethereal HCl. This material was twice recrystallized from a 20:1 solution of ethyl acetate/methanol to yield 7,8-dimethoxy-3-methyl-2,3,4,5-tetrahydro-1-(p-trifluoromethylphenoxy)-3-benzazepine hydrochloride, d 204°–205° C.

ANALYSIS: Calculated for C$_{20}$H$_{22}$F$_3$NO$_3$.HCl: 57.49%C, 5.55%H, 3.35%N, Found: 57.55%C, 5.64%H, 3.29%N.

EXAMPLE 21 a.

3-Cyanomethyl-7,8-dimethoxy-2,3,4,5-tetrahydro-1-(p-trifluoromethylphenoxy)-3-benzazepine A mixture of 7,8-dimethoxy-2,3,4,5-tetrahydro-1-(p-trifluoromethylphenoxy)-3-benzazepine (11 g, 0.030 mole), chloroacetonitrile (4.5 g, 0.060 mole) and sodium bicarbonate (10 g, 0.12 mole) in DMF (125 ml) was stirred at 75°–80° C. for two hours. The mixture was concentrated to an oil which was stirred with water and extracted with ethyl acetate-ether. The organic layers were washed twice with water and dried (saturated NaCl, anhydrous MgSO$_4$). The solution was filtered and concentrated to an oil (12 g, 95%) which was extracted with boiling hexanes to yield a solid (7 g, m.p. 83°–88° C.). A sample was recrystallized from hexanes to yield 3-cyanomethyl-7,8-dimethoxy-2,3,4,5-tetrahydro-1-(p-trifluoromethylphenoxy)-3-benzazepine, m.p. 93°–94° C.

ANALYSIS: Calculated for C$_{21}$H$_{21}$F$_3$N$_2$O$_3$: 62.06%C, 5.21%H, Found: 61.79%C, 5.14%H.

b.

3-(2-Aminoethyl)-7,8-dimethoxy-2,3,4,5-tetrahydro-1-(p-trifluoromethylphenoxy)-3-benzazepine dioxalate A solution of 3-cyanomethyl-7,8-dimethoxy-2,3,4,5-tetrahydro-1-(p-trifluoromethylphenoxy)-3-benzazepine of Example 21a (12 g, 0.030 mol) in THF (100 ml) was dropped into a stirred suspension of LiAlH$_4$ (4.6 g, 0.12 mole) in THF (200 ml). After stirring at reflux for four hours, the mixture was cooled, diluted with ether, then quenched by dropwise addition of saturated NH$_4$Cl (20 ml). The mixture was filtered, washed twice with water and dried (saturated NaCl, anhydrous MgSO$_4$). The solution was filtered, then concentrated to an oil (9.2 g, 75%) which was dissolved in ether and converted to the dioxalate salt (11 g, d 130°–135° C.) using the procedure of Example 1. 4.0 g, of material was twice recrystallized from methanol/ether to yield 3-(2-aminoethyl)-7,8-dimethoxy-2,3,4,5-tetrahydro-1-(p-trifluoromethylphenoxy)-3-benzazepine dioxalate, d 139°–140° C.

ANALYSIS: Calculated for C$_{21}$H$_{25}$F$_3$N$_2$O$_3$.2-(CO$_2$H)$_2$: 50.85%C, 4.95%H, Found: 50.70%C, 4.94%H.

EXAMPLE 22

1-(m-Chlorophenoxy)-7,8-dimethoxy-2,3,4,5-tetrahydro-3-benzazepine oxalate

A solution of 7,8-dimethoxy-1-hydroxy-2,3,4,5-tetrahydro-3-benzazepine (6.5 g, 0.029 mole) in DMF (50 ml) was added at room temperature to a suspension of sodium hydride (1.7 g, 50% oil dispersion, 0.034 mole, washed twice with hexane) in DMF (10 ml). The mixture was warmed to 70° C. for one hour, then was cooled to 50° C., and a solution of 1-chloro-3-fluorobenzene (4.6 g, 0.034 mole) in DMF (10 ml) was slowly added. After stirring four hours, the mixture was cooled, then concentrated to an oil which was stirred with water and extracted with ethyl acetate. The organic extracts were washed twice with water, then dried (saturated NaCl, anhydrous MgSO$_4$). The solution was filtered then concentrated to an oil (8 g, 82%), which was purified by column chromatography (silica gel, eluted with 20% C$_2$H$_5$OH/CHCl$_3$) to yield an oil (2.0 g) which was converted to the oxalate salt, using the procedure of Example 1 (2.3 g, d 130°–140° C.), then recrystallized from a 25:1 solution of ethyl acetate/methanol to yield 1-(m-chlorophenoxy)-7,8-dimethoxy-2,3,4,5-tetrahydro-3-benzazepine oxalate (2.0 g, d 177°–178° C.).

ANALYSIS: Calculated for $C_{18}H_{20}ClNO_3.(CO_2H)_2$: 56.67%C, 5.23%H, Found: 56.52%C, 5.16%H.

EXAMPLE 23 a.
3-(2-Ethoxycarbonylaminoethyl)-2,3,4,5-tetrahydro-1-(p-trifluoromethylphenoxy)-3-benzazepine To a cooled solution of 3-(2-aminoethyl)-2,3,4,5-tetrahydro-1-(p-trifluoromethylphenoxy)-3-benzazepine of Example 21b (5.5 g, 0.016 mole) and triethylamine (1.8 g, 0.018 mole) in chloroform (75 ml) was slowly dropped a solution of ethyl chloroformate (2.0 g, 0.018 mole) in chloroform (25 ml). After stirring twenty hours at ambient temperature the reaction mixture was concentrated to a semisolid which was dissolved in ether, washed with water and dried (saturated NaCl, anhydrous $MgSO_4$). The solution was filtered and concentrated to yield an oil. A sample of the resultant oil was distilled to yield an oil of 3-(2-ethoxycarbonylaminoethyl)-2,3,4,5-tetrahydro-1-(p-trifluoromethylphenoxy)-3-benzazepine, bp 235°–238° C./0.10 mm.

ANALYSIS: Calculated for $C_{22}H_{25}F_3N_2O_3$: 62.55%C, 5.97%H, Found: 62.69%C, 5.88%H.

b.
3-(2-Methylaminoethyl)-2,3,4,5-tetrahydro-1-(p-trifluoromethylphenoxy)-3-benzazepine dioxalate A solution of 3-(2-ethoxycarbonylaminoethyl)-2,3,4,5-tetrahydro-1-(p-trifluoromethylphenoxy)-3-benzazepine of Example 23a (5.0 g, 0.012 mole) in THF (75 ml) was slowly dropped into a stirred suspension of $LiAlH_4$ (0.9 g, 0.024 mole) in THF (25 ml). After refluxing two hours, the reaction mixture was cooled, diluted with ether, then quenched by dropwise addition of saturated $NH_4Cl$ (25 ml). The mixture was filtered, and the organic filtrate was washed twice with water and dried (saturated NaCl, anhydrous $MgSO_4$). The solution was filtered, then concentrated to an oil (4.9 g) which was converted using the procedure of Example 1 to the dioxalate salt (6 g, 92%, d 199°–201° C.). This material was twice recrystallized from methanol to yield 3-(2-methylaminoethyl)-2,3,4,5-tetrahydro-1-(p-trifluoromethylphenoxy)-3-benzazepine dioxalate, d 207°–208° C.

ANALYSIS: Calculated for $C_{20}H_{23}F_3N_2O.2(CO_2H)_2$: 52.94%C, 5.00%H, Found: 53.05%C, 5.13%H.

EXAMPLE 24 a.
3-Cyanomethyl-2,3,4,5-tetrahydro-1-(m-trifluoromethylphenoxy)-3-benzazepine A mixture of 2,3,4,5-tetrahydro-1-(m-trifluoromethylphenoxy)-3-benzazepine of Example 6 (10 g, 0.033 mole), chloroacetonitrile (4.9 g, 0.065 mole) and sodium bicarbonate (11 g, 0.13 mole) in DMF (100 ml) was stirred at 55°–60° C. for three hours. The mixture was concentrated to an oil which was stirred with water and extracted with ether. The organic extracts were washed twice with water and dried (saturated NaCl, anhydrous, $MgSO_4$). The solution was filtered and concentrated to an oil (11 g, 96%) of which 3.8 g was distilled to yield 2.4 g. of an oil of 3-cyanomethyl-2,3,4,5-tetrahydro-1-(m-trifluoromethylphenoxy)-3-benzazepine (220°–223° C./0.10 mm).

ANALYSIS: Calculated for $C_{19}H_{17}F_3N_2O$: 65.88%C, 4.95%H, Found: 65.97%C, 4.99%H.

b.
3-(2-Aminoethyl)-2,3,4,5-tetrahydro-1-(m-trifluoromethylphenoxy)-3-benzazepine dioxalate A solution of 3-cyanomethyl-2,3,4,5-tetrahydro-1-(m-trifluoromethylphenoxy)-3-benzazepine of Example 24a (8 g, 0.023 mole) in THF (100 ml) was dropped into a stirred suspension of $LiAlH_4$ (3.5 g, 0.092 mole) in THF (100 ml) and stirred at ambient temperature for one hour. The mixture was then cooled, diluted with anhydrous ether, quenched by slow addition of saturated $NH_4Cl$, then was filtered, washed twice with water and was dried (saturated NaCl, anhydrous $MgSO_4$). The solution was then filtered and concentrated to an oil (6.8 g) which was converted using the procedure of Example 1 to the dioxalate salt (7.5 g, 50%, d 160°–163° C.). This material was twice recrystallized from a 25:1 ethyl acetate-methanol solution to a solid of 3-(2-aminoethyl)-2,3,4,5-tetrahydro-1-(m-trifluoromethylphenoxy)-3-benzazepine dioxalate, d 170°–171° C.

ANALYSIS: Calculated for $C_{19}H_{21}F_3N_2O.2(CO_2H)_2$: 52.07%C, 4.75%H, Found: 52.15%C, 4.86%H.

EXAMPLE 25

3-(2-Aminoethyl)-1-(m-chlorophenoxy)-2,3,4,5-tetrahydro-3-benzazepine dioxalate

A mixture of 1-(m-chlorophenoxy)-2,3,4,5-tetrahydro-3-benzazepine of Example 4 (8.0 g, 0.029 mole), chloroacetonitrile (4.4 g, 0.058 mole) and sodium bicarbonate (10 g, 0.12 mole in DMF (100 ml) was stirred at 65° C. for 2.5 hours. The mixture was concentrated to an oil which was stirred with water and extracted with ether. The organic extracts were washed twice with water and dried (saturated NaCl, anhydrous $MgSO_4$). The solution was filtered and concentrated to an oil (8 g) which was extracted with boiling hexanes and concentrated to a light solid (5.4 g, 62%, m.p. 89°–95° C.). A solution of 1-(m-chlorophenoxy)-3-cyanomethyl-2,3,4,5-tetrahydro-3-benzazepine (5.1 g, 0.017 mole) in THF (50 ml) was dropped into a stirred suspension of $LiAlH_4$ (2.6 g, 0.068 mole) in THF (100 ml). After stirring three hours at ambient temperature, the reaction mixture was cooled, diluted with ether, then quenched by dropwise addition of saturated $NH_4Cl$. The mixture was filtered, and the organic filtrate was washed twice with water and dried (saturated NaCl, anhydrous $MgSO_4$). The solution was filtered and concentrated to an oil (3.7 g,) which was converted using the procedure of Example 1 to the dioxalate salt (5.5 g, 65%, d 150°–155° C.). This material was twice recrystallized from a 20:1 solution of ethyl acetate/methanol to yield 3-(2-aminoethyl)-1-(m-chlorophenoxy)-2,3,4,5-tetrahydro-3-benzazepine dioxalate, d 172°–173° C.

ANALYSIS: Calculated for $C_{18}H_{21}ClN_2O.2(CO_2H)_2$: 53.17%C, 5.07%H, Found: 53.47%C, 5.12%H.

EXAMPLE 26

3-(2-Dimethylaminoethyl)-1-(p-trifluoromethylphenoxy)-3-benzazepine dihydrochloride A mixture of 2,3,4,5-tetrahydro-1-(p-trifluoromethylphenoxy)-3-benzazepine of Example 1 (8.5 g, 0.028 mole), 2-dimethylaminoethyl chloride hydrochloride (6.5 g, 0.045 mole) and sodium bicarbonate (18 g, 0.21 mole) in DMF (125 ml) was stirred at 60° C. for two hours. The reaction mixture was concentrated to a slurry which was stirred with water and extracted with ethyl acetate-ether. The organic extracts were washed twice with water and dried (saturated NaCl, anhydrous $MgSO_4$). The solution was filtered and concentrated to an oil (8 g) which was converted to the dihydrochloride salt (6 g, 48% d 179° C.) by the addition of ethereal HCl. This material was recrystallized twice from a 20:1 ethyl acetate/methanol solution to yield 3-(2-dimethylaminoethyl)-1-(p-trifluoromethylphenoxy)-3-benzazepine dihydrochloride, d 237°–238° C.

ANALYSIS: Calculated for $C_{21}H_{25}F_3N_2O.2HCl$: 55.88%C, 6.03%H, Found: 55.87%C, 5.94%H.

EXAMPLE 27 a.
3-(2-Cyanoethyl)-2,3,4,5-tetrahydro-1-(p-trifluoromethylphenoxy)-3-benzazepine A solution of 2,3,4,5-tetrahydro-1-(p-trifluoromethylphenoxy)-3-benzazepine of Example 1 (15 g, 0.049 mole) and acrylonitrile (5.2 g, 0.098 mole) in isopropanol (50 ml) was stirred at reflux (95° C.) for twenty hours. The reaction mixture was cooled then concentrated to an oil (17 g, 96%) of which 3.5 g was distilled to an oil of 3-(2-cyanoethyl)-2,3,4,5-tetrahydro-1-(p-trifluoromethylphenoxy)-3-benzezepine (2.6 g, 235°–237° C./0.1 mm).

ANALYSIS: Calculated for $C_{20}H_{19}F_3N_2O$: 66.65%C, 5.31%H, 7.78%N, Found: 66.75%C, 5.31%H, 7.78%N.

b.
3-(3-Aminopropyl)-2,3,4,5-tetrahydro-1-(p-trifluoromethylphenoxy)-3-benzazepine dimaleate A solution of 3-(2-cyanoethyl)2,3,4,5-tetrahydro-1-(p-trifluoromethylphenoxy)-3-benzazepine of Example 27a in THF (10 ml) was slowly dropped into a stirred solution of borane in THF (20 mmole, 20 ml), cooled with an ice bath. After the addition was completed, the reaction mixture was stirred at ambient temperature overnight (about 16 hours). The mixture was cooled and quenched by slow addition of HCl (3N, 25 ml) and then refluxed for thirty minutes. The reaction mixture was again cooled, diluted with water, basified with saturated sodium carbonate and extracted with ether. The organic extract was washed twice with water and dried (saturated NaCl, anhydrous $MgSO_4$). The solution was filtered and concentrated to an oil (3 g) which was dissolved in ether, then converted to the dimaleate salt by the addition of an ethereal-maleic acid solution (5 g, 95%, m.p. 145°–149° C.). This material was recrystallized from ethyl acetate[methanol] to yield 2.8 g of 3-(3-aminopropyl)-2,3,4,5-tetrahydro-1-(p-trifluoromethylphenoxy)-3-benzazepine dimaleate, d 164°–165° C.

ANALYSIS: Calculated for $C_{20}H_{23}F_3N_2O.2(C_4H_4O_4)$: 56.37%C, 5.24%H, Found: 56.35%C, 5.15%H.

EXAMPLE 28 a.
1-Phenoxy-2,3,4,5-tetrahydro-3-(p-toluenesulfonyl)-3-benzazepine

To a solution of 1-hydroxy-2,3,4,5-tetrahydro-3-(p-toluenesulfonyl)-3-benzazepine (10 g, 32 mmole), phenol (3.4 g, 36 mmole) and triphenylphosphine (9.5 g, 36 mmole) in benzene (300 ml), cooled with an ice bath, was slowly dropped a solution of diethyl azodicarboxylate (6.3 g, 36 mmole) in benzene (100 ml). After stirring twenty hours at ambient temperature, the reaction mixture was filtered to removed sym-dicarbethoxyhydrazine. The filtrate was concentrated to an oil which was dissolved in ether and cooled to precipitate the product and triphenylphosphine oxide. The desired product was crystallized from methanol to give a solid of 1-phenoxy-2,3,4,5-tetrahydro-3-(p-toluenesulfonyl)-3-benzazepine (6.8 g, 33%, m.p. 155°–156° C.).

ANALYSIS: Calculated for $C_{23}H_{23}NO_3S$: 70.20%C, 5.89%H, Found: 69.94%C, 5.93%H.

b. 1-Phenoxy-2,3,4,5-tetrahydro-3-benzazepine hydrochloride

A solution of 1-phenoxy-2,3,4,5-tetrahydro-3-(p-toluenesulfonyl)-3-benzazepine of Example 28 a (3.0 g, 7.6 mmole) in toluene (10 ml) was added to a solution of sodium bis (2-methoxyethoxy) aluminum hydride (9.2 g, 45.6 mmole, 70% in toluene) and stirred four days at ambient temperature. The reaction mixture was warmed at 60° C. for three hours then was stirred at ambient temperature for twenty hours. The reaction mixture was then cooled, quenched by slow addition of 10% NaOH and separated. The organic layer was washed with water, dried, filtered and concentrated to an oil (1.9 g). The resultant oil was converted to the hydrochloride salt by the addition of ethereal HCl. This material was immediately recrystallized from a 20:1 solution of ethyl acetate/methanol to yield a solid of 1-phenoxy-2,3,4,5-tetrahydro-3-benzazepine hydrochloride (1.4 g, 67%, m.p. 218°–220° C.).

ANALYSIS: Calculated for $C_{16}H_{17}NO.HCl$: 69.68%C, 6.58%H, Found: 69.43%C, 6.63%H.

EXAMPLE 29 a.
1-(p-Methylphenoxy)-2,3,4,5-tetrahydro-3-(p-toluenesulfonyl)-3-benzazepine To a solution of 1-hydroxy-2,3,4,5-tetrahydro-3-(p-toluenesulfonyl)-3-benzazepine (18 g, 57 mmole), p-cresol (7 g, 68 mmole) and triphenylphosphine (18 g, 68 mmole) in 300 ml benzene, cooled with an ice bath, was slowly dropped a solution of diethyl azodicarboxylate (12 g, 68 mmole) in 100 ml benzene. After stirring twenty hours at ambient temperature, the reaction mixture was filtered to remove sym-dicarbethoxyhydrazine (10 g, 83%, m.p. 132°–135° C.) then evaporated to an oil which was purified by column chromatography (silica gel, dichloromethane) to give 16 g of an oil. This oil was purified by high pressure liquid chromatography (silica gel, 30% hexane in toluene) to give 10 g of product. This material was crystallized from hexane-ether to give 8 g (35%) of 1-(p-methylphenoxy)-2,3,4,5-tetrahydro-3-(p-toluenesulfonyl)-3-benzazepine, m.p. 84°–86° C.

Calculated for $C_{24}H_{25}NO_3S$: 70.73%C, 6.18%H, Found: 70.57%C, 6.30%H.

b.
1-(p-Methylphenoxy)-2,3,4,5-tetrahydro-3-benzazepine oxalate

A solution of 1-(p-methylphenoxy)-2,3,4,5-tetrahydro-3-(p-toluenesulfonyl)-3-benzezepine of Example 29a (3 g, 7.4 mmole) in toluene (15 ml) was added to a solution of sodium bis (2-methoxyethoxy) aluminum hydride (8.9 g, 44.2 mmole, 70% in toluene), and stirred four days at ambient temperature. The reaction mixture was diluted with ether, quenched by slow addition of 10% NaOH (10 ml) and was separated. The organic layer was washed with water, dried (saturated NaCl, anhydrous MgSO$_4$), filtered and concentrated to an oil (2.2 g) which was converted utilizing the procedure of Example 1 to the oxalate salt (1.4 g. 55%, d 219° C.). This material was recrystallized from a 20:1 solution of ethyl acetate/methanol to yield 1-(p-methylphenoxy)-2,3,4,5-tetrahydro-3-benzazepine oxalate, d 222°-223° C.

ANALYSIS: Calculated for $C_{17}H_{19}NO.(CO_2H)_2$: 66.46%C, 6.16%H, Found: 66.20%C, 6.15%H.

EXAMPLE 30 a.
1-(p-Methoxyphenoxy)-2,3,4,5-tetrahydro-3-(p-toluenesulfonyl)-3-benzazepine To a solution of 1-hydroxy-2,3,4,5-tetrahydro-3-(p-toluenesulfonyl)-3-benzazepine (15 g, 47 mmole), p-methoxyphenol (7 g, 57 mmole) and triphenylphosphine (15 g, 57 mmole) in 300 ml benzene, cooled with an ice bath, was slowly dropped a solution of diethyl azodicarboxylate (10 g, 57 mmole) in 100 ml benzene. After stirring two hours at ambient temperature, the reaction mixture was filtered to remove sym-dicarbethoxyhydrazine (8 g, 96%, m.p. 130°-132° C.), then evaporated to an oil which was purified by column chromatography (silica gel, dichloromethane) to give an oil. This oil was crystallized from hexane-ether to give 6 g (30%) of 1-(p-methoxyphenoxy)-2,3,4,5-tetrahydro-3-(p-toluenesulfonyl)-3-benzazepine, m.p. 84°-85° C.

Calculated for $C_{24}H_{25}NO_4S$: 68.06%C, 5.95%H, Found: 68.13%C, 5.85%H.

b.
1-(p-Methoxyphenoxy)-2,3,4,5-tetrahydro-3-benzazepine oxalate

A solution of 1-(p-methoxyphenoxy)-2,3,4,5-tetrahydro-3-(p-toluenesulfonyl)-3-benzazepine of Example 30a (5.0 g, 11.8 mmole) in toluene (30 ml) was added to a solution of sodium bis (2-methoxyethoxy) aluminum hydride (14.3 g, 70.8 mmole, 70% in toluene) and stirred at ambient temperaure twenty hours. The reaction mixture was diluted with ether, quenched by slow addition of 10% NaOH and separated. The organic layer was washed with water, dried, filtered and concentrated to an oil which was converted using the procedure of Example 1 to the oxalate salt (1.2 g, 28%, d 186°-188° C.). This material was recrystallized from a 20:1 solution of ethyl acetate/methanol to give a solid of 1-(p-methoxyphenoxy)-2,3,4,5-tetrahydro-3-benzazepine oxalate, d 201°-202° C.

ANALYSIS: Calculated for $C_{17}H_{19}NO_2.(CO_2H)_2$: 63.50%C, 5.89%H, Found: 63.22%C, 5.88%H.

EXAMPLE 31

3-Methyl-1-phenoxy-2,3,4,5-tetrahydro-3-benzazepine hydrochloride

To a cooled solution of 1-phenoxy-2,3,4,5-tetrahydro-3-benzazepine (3.9 g, 16 mmole) of Example 28b and triethylamine (1.8 g, 18 mmole) in chloroform (50 ml) was slowly added ethyl chloroformate (1.9 g, 18 mmole) in chloroform (10 ml). The reaction mixture was stirred two hours at ambient temperature, then was evaporated to an oil which was stirred with water and extracted with ether. The organic extracts were washed with dilute HCl, water, then dried (saturated NaCl, anhydrous MgSO$_4$). The solution was filtered and concentrated to an oil (4.7 g, 93%). A solution of the oil in THF (40 ml) was slowly added to a cooled suspension of LiAlH$_4$ (1.7 g, 45 mmole) in THF (100 ml). After stirring three hours at ambient temperature, the mixture was cooled, diluted with ether, then quenched by slow addition of saturated NH$_4$Cl. The mixture was filtered, washed with water and dried (saturated NaCl, anhydrous MgSO$_4$). The solution was filtered and concentrated to an oil which was converted by the addition of ethereal HCl to the hydrochloride salt (3 g 69%, d 211°-214° C.). This material was recrystallized from a 20:1 solution of ethyl acetate/methanol to yield 3-methyl-1-phenoxy-2,3,4,5-tetrahydro-3-benzazepine hydrochloride, d 224°-225° C.

ANALYSIS: Calculated for $C_{17}H_{19}NO.HCl$: 70.45%C, 6.96%H, Found: 70.18%C, 7.04%H.

EXAMPLE 32

3-(2-Amino-1-methyl)ethyl-2,3,4,5-tetrahydro-1-(p-trifluoromethylphenoxy)-3-benzazepine dioxalate A mixture of 2,3,4,5-tetrahydro-1-(p-trifluoromethylphenoxy)-3-benzazepine (6.5 g, 21 mmole), 2-chloropropionamide (4.5 g, 42 mmole), sodium bicarbonate (20 g) and 0.01 g of potassium iodide in DMF (80 ml) was stirred at 85° C. for twenty hours. The reaction mixture was cooled and evaporated to a semisolid which was stirred with water and extracted with ether. The ether extracts were washed twice with water, dried (saturated NaCl, anhydrous MgSO$_4$), filtered and concentrated to an oil (8 g). A solution of the oil (8 g, 21 mmole) in THF (100 ml) was slowly added to a solution of borane in THF (1.01M, 63 mmole), cooled with an ice bath. The solution was stirred at ambient temperature for twenty hours, then at 70° C. for two hours. The mixtures was cooled, acidified with 3N HCl and refluxed for one hour. The reaction mixture was again cooled, basified with 3N NaOH and extracted with ether. The ether extracts were washed twice with water, dried (saturated NaCl, anhydrous MgSO$_4$), filtered and concentrated to an oil (7 g), which was converted using the procedure of Example 1 to the dioxalate salt (9 g, 79%, d 80°-90° C.). This material was recrystallized from an ethyl acetate/ether solution to yield 3-(2-amino-1-methyl)ethyl-2,3,4,5-tetrahydro-1-(p-trifluoromethylphenoxy)-3-benzazepine dioxalate, d 105° C.

ANALYSIS: Calculated for $C_{20}H_{23}F_3N_2O.2(CO_2H)_2$: 52.94%C, 5.00%H, Found: 53.26%C, 5.14%H.

EXAMPLE 33

1-(p-Methoxyphenoxy)-3-methyl-2,3,4,5-tetrahydro-3-benzazepine hydrobromide 1-(p-Methoxyphenoxy)-2,3,4,5-tetrahydro-3-benzazepine of Example 30b (4 g, 15 mmole) was dissolved in 4.5 ml cold 97% formic acid and to this was added 4 ml 37% formaldehyde solution. After stirring at 95° C. for four hours, the reaction mixture was cooled, acidified with 30 ml dilute HCl and warmed at 70° C. for one hour. The reaction mixture was then cooled, basified with dilute NaOH and extracted with ether. The extracts were washed with water, dried (saturated NaCl, anhydrous MgSO$_4$), filtered and concentrated to an oil (3.7 g, 88%) which was distilled to yield an oil (3.2 g, b.p. 173°–175°/0.3 mm). This oil was converted by the addition of ethereal HBr to 1-(p-methoxyphenoxy)-3-methyl-2,3,4,5-tetrahydro-3-benzazepine hydrobromide (3.2 g, d 205°–206° C.).

ANALYSIS: Calculated for $C_{18}H_{21}NO_2 \cdot HBr$: 59.35%C, 6.09%H, Found: 59.21%C, 6.06%H.

EXAMPLE 34

3-Methyl-1-(p-methylphenoxy)-2,3,4,5-tetrahydro-3-benzazepine Hydrobromide 1-(p-Methylphenoxy)-2,3,4,5-tetrahydro-3-benzazepine of Example 29b (1.3 g, 5.1 mole) was dissolved in 4.5 ml cold 97% formic acid and to this was added 4 ml 37% formaldehyde solution. After stirring at 95° C. for one hour, the reaction mixture was cooled, acidified with 15 ml dilute HCl and warmed at 70° C. for 30 minutes. The reaction mixture was then cooled, basified with dilute NaOH and extracted with ether. The organic extracts were washed with water, dried (saturated NaCl, anhydrous MgSO$_4$), filtered and concentrated to an oil which was converted by the addition of ethereal HBr to the hydrobromide salt. This material was recrystallized from a 20:1 solution of ethyl acetate/methanol to yield 3-methyl-1-(p-methylphenoxy)-2,3,4,5-tetrahyro-3-benzazepine hydrobromide (1.5 g, 84%, d 206°–207° C.).

ANALYSIS: Calculated for $C_{18}H_{21}NO \cdot HBr$: 62.07%C, 6.37%H, Found: 61.62%C, 6.40%H.

EXAMPLE 35

7,8-Dimethoxy-1-phenoxy-2,3,4,5-tetrahydro-3-benzazepine oxalate

To a solution of 7,8-dimethoxy-1-hydroxy-2,3,4,5-tetrahydro-3-(p-toluenesulfonyl)-3-benzazepine (15 g, 40 mmole), phenol (3.6 g, 40 mmole) and triphenylphosphine (10.8 g, 41 mmole) in benzene (400 ml), cooled with an ice bath, was slowly dropped a solution of diethyl azodicarboxylate (7.2 g, 42 mmole) in benzene (100 ml). After stirring three hours at ambient temperature, the reaction mixture was filtered to remove sym-dicarbethoxyhydrazine (6.2 g, 94%, m.p. 132°–134° C.), then was concentrated to an oil (35 g) which was purified by column chromatography (silica gel, ether) to give 16 g, (88%) of an oil. A solution of the resultant 7,8-dimethoxy-1-phenoxy-2,3,4,5-tetrahydro-3-(p-toluenesulfonyl)-3-benzazepine (15 g, 33 mmole) in toluene (65 ml) was added to a solution of sodium bis (2-methoxyethoxy) aluminum hydride (40 g, 0.2 mole, 70% in toluene). The reaction mixture was stirred at ambient temperature for two days, then at 70° C. for three hours. The reaction mixture was then cooled and poured slowly into 1 liter of dilute NaOH and extracted with ethyl acetate. The organic extracts were washed twice with water, dried (saturated NaCl, anhydrous MgSO$_4$), filtered and converted utilizing the procedure of Example 1 to the oxalate salt (8 g, 62%, m.p. 100° C.). This material was recrystallized from a 20:1 solution of ethyl acetate/methanol to give 7,8-dimethoxy-1-phenoxy-2,3,4,5-tetrahydro-3-benzazepine oxalate, d 148°–149° C.

ANALYSIS: Calculated for $C_{L9}H_{23}NO_3 \cdot (CO_2H)_2$: 61.68%C, 5.95%H, Found: 61.32%C, 5.97%H.

EXAMPLE 36

7,8-Dimethoxy-3-methyl-1-phenoxy-2,3,4,5-tetrahydro-3-benzazepine oxalate

To a cooled solution of 7,8-dimethoxy-1-phenoxy-2,3,4,5-tetrahydro-3-benzazepine of Example 35 (3.8 g, 13 mmole) and triethylamine (1.5 g, 15 mmole) in chloroform (50 ml) was slowly dropped a solution of ethyl chloroformate (1.6 g, 15 mmole) in chloroform (10 ml). The reaction mixture was stirred twenty hours at ambient temperature, then was concentrated to an oil which was dissolved in ethyl acetate-ether and washed with dilute HCl, water and then dried (saturated NaCl, anhydrous MgSO$_4$). The solution was filtered and concentrated to give 4 g of an oil (85%). A solution of the oil (4 g, 11 mmole) in THF (40 ml) was slowly added to a suspension of LiAlH$_4$ (0.8 g, 22 mmole) in THF (100 ml). After stirring twenty hours at ambient temperature, the reaction mixture was diluted with ether, quenched by slow addition of saturated NH$_4$Cl and then was filtered. The organic filtrate was washed twice with water, dried (saturated NaCl, anhydrous MgSO$_4$), filtered and concentrated to give 3.1 g of an oil. This oil was purified by column chromatography (silica gel, THF) to give 2.3 g of an oil (67%). This oil was converted using the procedure of Example 1 to the oxalate salt and recrystallized from a 20:1 solution of ethyl acetate/methanol to give 1.8 g of a solid, m.p. 160° C. This material was again recrystallized from a 20:1 solution of ethyl acetate/methanol to give 1.5 g of 7,8-dimethoxy-3-methyl-1-phenoxy-2,3,4,5-tetrahydro-3-benzazepine oxalate, d 169°–170° C.

ANALYSIS: Calculated for $C_{19}H_{23}NO_3 \cdot (CO_2H)_2$: 62.52%C, 6.25%H, Found: 62.18%C, 6.15%H.

EXAMPLE 37

7.8-Dimethoxy-3-ethyl-2,3,4,5-tetrahydro-1-(p-trifluoromethylphenoxy)-3-benzazepine hydrochloride To a solution of 7,8-dimethoxy-2,3,4,5-tetrahydro-1-(p-trifluoromethylphenoxy)-3-benzazepine (5.5 g, 15 mmole), the compound of Example 19, and triethylamine (1.8 g, 18 mmole) in chloroform (70 ml), cooled with an ice bath, was slowly added a solution of acetyl chloride (1.4 g, 18 mmole) in chloroform (30 ml). After one hour, the mixture was concentrated to a semi-solid which was stirred with water and extracted with ethyl acetate-ether. The organic extracts were washed with dilute HCl, water then dried (saturated NaCl, anhydrous MgSO$_4$). The solution was filtered and concentrated to an oil (5 g. 82%). A solution of the oil (5 g, 12 mmole) in THF (40 ml) was slowly added to a suspension of LiAlH$_4$ (0.9 g, 24 mmole) in THF (100 ml), cooled with an ice bath. After on hour the mixture was quenched by slow addition of saturated NH$_4$Cl, then was filtered. The filtrate was washed twice with water, dried (saturated NaCl, anhydrous MgSO$_4$), filtered and concentrated to give 5 g of an oil which was purified by column chromatography (silica gel, THF) to give 3.9 g of an oil. This material was converted by the addition the ethereal HCl to the hydrochloride salt and recrystallized from a 20:1 solution of ethyl acetate/methanol to give 3 g (57%) of a solid, d 180°–185° C. This material was again recrystallized to give 7,8-dimethoxy-3-ethyl-2,3,4,5-tetrahydro-1-(p-trifluoromethylphenoxy)-3-benzazepine hydrochloride, d 185°–186° C.

ANALYSIS: Calculated for $C_{21}H_{24}F_3NO_3 \cdot HCl$: 58.40%C, 5.84%, Found: 58.10%C, 5.80%H.

EXAMPLE 38

7,8-Dimethoxy-1-(4-methoxyphenoxy)-3-methyl-2,3,4,5-tetrahydro-3-benzazepine hydrochloride To a solution of 7,8-dimethoxy-1-hydroxy-2,3,4,5-tetrahydro-3-(p-toluenesulfonyl)-3-benzazepine (27 g, 72 mmole), p-methoxyphenol (9 g, 72 mmole) and triphenylphosphine (23 g, 86 mmole) in benzene (300 ml), cooled with an ice bath, was slowly dropped a solution of diethyl azodicarboxylate (15 g, 86 mmole) in benzene (100 ml). After stirring twenty hours at ambient temperature, the reaction mixture was filtered to remove sym-dicarbethoxyhydrazine (11,4 g, 90% m.p. 132°–4° C.) then concentrated to an oil (65 g) which was purified by column chromatography (silica gel, dichloromethane) to give 27 g (78%) of an oil. The resulting 7,8-dimethoxy-1-(4-methoxyphenoxy)-2,3,4,5-tetrahydro-3-(p-toluenesulfonyl)-3-benzazepine (17 g, 35 mmole) in toluene (30 ml) was added to a solution of sodium bis (2-methoxyethoxy)aluminum hydride (70 g, 0.35 mole, 70% in toluene). The reaction mixture was stirred at ambient temperature for three days, then was diluted with toluene and quenched by slow addition of 10% NaOH. The mixture was filtered and the organic filtrate was washed twice with water, dried (saturated NaCl, anhydrous MgSO4), filtered and concentrated to an oil which was converted to the oxalate salt, as by the procedure of Example 1, then immediately rebasified to give 7 g, (60%) of an oil. The resulting 7,8-dimethoxy-1-(4-methoxyphenoxy)-2,3,4,5-tetrahydro-3-benzazepine (7 g, 21 mmole) was dissolved in 9 ml cold 88% formic acid and to this was added 8 ml 33% formaldehyde solution. The mixture stirred at 90° C. for two hours, then was cooled, diluted with water and basified with sodium carbonate. The oil which separated was extracted with ethyl acetate-ether then was washed twice with ether, dried (saturated NaCl, anhydrous MgSO4), filtered and concentrated to an oil which was converted to the hydrochloride salt (6.7 g, 84%, m.p. 130°–140° C.). This material was recrystallized from a 20:1 solution of ethyl acetate/methanol to give 7,8-dimethoxy-1-(4-methoxyphenoxy)-3-methyl-2,3,4,5-tetrahydro-3-benzazepine hydrochloride, (4.1 g, m.p. 197°–198° C.).

ANALYSIS: Calculated for $C_{20}H_{25}NO_4 \cdot HCl$: 63.23%C, 6.90%H, Found: 63.20%C, 6.89%H.

EXAMPLE 39

3-(p-Toluenesulfonyl)-1-(4-trifluoromethylphenoxy)-2,3,4,5-tetrahydro-3-benzazepine A solution of 1-hydroxy-3-(p-toluenesulfonyl)-2,3,4,5-tetrahydro-3-benzazepine (28.56 g, 0.89 mole) in dry DMF (180 ml) was added dropwise at room temperature under nitrogen to a vigorously stirred suspension of NaH (4.85 g, 50% of 98% in oil, 0.099 mole, washed twice with hexane) in DMF (135 ml). After the addition was completed, the mixture was warmed briefly to 60° C., then cooled to room temperature. To this mixture was added rapidly dropwise a solution of p-fluorobenzotrifluoride (15.51 g, 0.0945 mole) in DMF (90 ml). After stirring at room temperature for 24 hours the reaction mixture was warmed briefly to 55° C., then allowed to cool slowly to room temperature. This mixture was poured into water (3 l.) and extracted with methylene dichloride. The methylene dichloride solution was washed twice with water, saturated sodium chloride, treated with charcoal and filtered through Celite to give a colored solution. The aqueous portion was extracted several more times with ether, and this ether extract treated similarly to the methylene dichloride extract. The combined extracts yielded 38 g, of an oil (91.5%), which was chromatographed on 500 g of silica gel and eluted with methylene dichloride to yield 23.81 g (57%) of product, which crystallized from ether to yield 3-(p-toluenesulfonyl)-1-(4-trifluoromethylphenoxy)-2,3,4,5-tetrahydro-3-benzazepine product, m.p. 114°–115° C. Recrystallization from hexane gave product, m.p. 115°–117° C.

ANALYSIS: Calculated for $C_{24}H_{22}F_3NO_3S$: 62.45%C, 4.81%H, 3.03%N, Found: 62.29%C, 4.81%H 2.94%M.

It is predicted that if the resultant 3-p-toluenesulfonyl-1-(4-trifluoromethylphenoxy)-2,3,4,5-tetrahydro-3-benzazepine of Example 39 is reacted with sodium bis (2-methoxyethoxy)aluminum hydride, and then methylated in the manner described in Example 38, that the compound of the invention, also described in 11b, 1-(4-trifluoromethylphenoxy)-3-methyl-2,3,4,5-tetrahydro-3-benzazepine will be obtained.

EXAMPLE 40

1-(4-Chlorophenoxy)-3-(p-toluenesulfonyl)-2,3,4,5-tetrahydro-3-benzazepine

A solution of 1-hydroxy-3-(p-toluenesulfonyl)-2,3,4,5-tetrahydro-3-benzazepine (5.8 g, 18.27 mmole) in DMF (40 ml) was added at room temperature to a suspension of sodium hydride (1 g of 50% oil dispersion, 20.098 mmol) (washed twice with hexane) in DMF (25 ml). After stirring fifteen minutes at room temperature the mixture was warmed briefly to 80° C., cooled to 65° C., then a solution of p-chlorofluorobenzene (2.5 g, 19.18 mmol) in DMF (25 ml) was added. After three days at room temperature, the temperature was raised to 80° C. for 24 hours. After an additional 24 hours at 100°–120° C. an additional 0.5 g of 99% NaH and 1 g of p-chlorofluorobenzene was added, and heating continued for 12 hours. Most of the DMF was removed under vacuum, the residue was poured onto ice and extracted with ether. The ether solution was dried and the ether removed to give 6.1 g of an oil (78%). The oil was dissolved in ether-hexane and on standing gave 2 g of a solid (25.6%). Trituration with methanol gave 1.5 g of a solid (19%). Recrystallization from methanol gave 1.17 g of a solid, m.p. 110°–112° C. The solid was again dissolved in hot methanol, cooled to room temperature and filtered through Celite. From the filtrate crystallized 0.83 g of 1-(4-chlorophenoxy)-3-(p-toluenesulfonyl)-2,3,4,5-tetrahydro-3-benzazepine, m.p. 116°–118° C. (11%).

ANALYSIS: Calculated for $C_{23}H_{22}ClNO_3S$: 64.54%C, 5.19%H, 3.27%N, Found: 64.60%C, 5.20%H, 3.11%N.

It is predicted that if the resultant 1-(4-chlorophenoxy)-3-(p-toluenesulfonyl)-2,3,4,5-tetrahydro-3-benzazepine of Example 40 is reacted with sodium bis (2- methoxyethyoxy)aluminum hydride and then methylated in the manner described in Example 38, that the compound 1-(4-chlorophenoxy)-3-methyl-2,3,4,5-tetrahydro-3-benzazepine will be obtained.

EXAMPLE 41

3-(p-Toluenesulfonyl)-1-(3-trifluoromethylphenoxy)-2,3,4,5-tetrahydro-3-benzazepine A solution of 1-hydroxy-3-(p-toluenesulfonyl)-2,3,4,5-tetrahydro-3-benzazepine (7.14 g, 0.0225 mole) in DMF (45 ml) was added dropwise at room temperature to a suspension of sodium hydride (1.21 g of 50% oil dispersion, 98%), previously washed twice with hexane, in DMF (35 ml). The mixture was stirred at room temperature for ½ hours, then warmed briefly to 70° C. and slowly cooled to room temperature. A solution of m-fluorobenzotrifluoride (3.9 g) in DMF (25 ml) was added rapidly dropwise, and the mixture stirred at room temperature for two days. The reaction mixture was heated overnight, about 16 hours, at 65°–70° C. An additional 0.5 g of 99% NaH and 1g of m-fluorobenzotrifluoride was added, and the mixture heated at 100° C. for about 4 hours. The mixture was cooled to room temperature, diluted with benzene, then most of the solvent was removed under vacuum. The residue was poured onto ice and extracted with ether. The ether solution was washed with water and dried and the solvent removed to give 7.5 g of an oil (72%). This was dissolved in ether and hexane and allowed to stand at room temperature to give 6.3 g (61%) of a solid, m.p. 105°–111° C. Recrystallization from methanol gave 4.64 g of crystalline material with the same melting point. A final product was obtained by chromatographing 4.15 g on silica gel (90 g) with methylene dichloride, and crystallizing the product from ether-petroleum ether to give 3.94 g of 3-(p-toluenesulfonyl)-1-(3-trifluoromethylphenoxy)-2,3,4,5-tetrahydro-3-benzazepine, m.p. 112°–113.5° C. (40% yield).

ANALYSIS: Calculated for $C_{24}H_{22}F_3NO_3S$: 62.45%C, 4.81%H, 3.03%N, Found: 62.11%C, 4.97%H, 2.91%N.

It is predicted that if the 3-(p-toluenesulfonyl)-1-(3-trifluoromethylphenoxy)-2,3,4,5-tetrahydro-3-benzazepine of Example 41 is reacted with sodium bis (2-methoxyethoxy) aluminum hydride and then methylated, in the manner described in Example 38, that the compound 3-methyl-1-(3-trifluoromethylphenoxy)-2,3,4,5-tetrahydro-3-benzazepine will be obtained.

EXAMPLE 42

7,8-Dimethoxy-1-(4-fluorophenoxy)-2,3,4,5-tetrahydro-3-benzazepine maleate

To a solution of 7,8-dimethoxy-1-hydroxy-2,3,4,5-tetrahydro-1-(p-toluenesulfonyl)-3-benzazepine (10 g, 26 m mole), 4-fluorophenol (3 g, 26 m mole) in 200 ml benzene, cooled with an ice bath, was slowly dropped a solution of diethyl azodicarboxylate (4.8 g, 28 m mole) in 60 mol benzene. After stirring two days at ambient temperature, the reaction mixture was filtered to remove sym-dicarbethoxyhydrazine (4 g, 86%, mp 132°–134° C.), then evaporated to 24 g of an oil which was purified by high pressure liquid chromatography (HPLC), [silica gel, dichloromethane] to give 9 g (71%) of a viscous oil. A solution of 7,8-dimethoxy-1-(4-fluorophenoxy)-2,3,4,5-tetrahydro-3-(p-toluenesulfonyl)-3-benzazepine (9 g, 19 m mole) in sodium bis (2-methoxyethoxy) aluminum hydride (3,4 M in toluene, 100 ml, 0.4 mole) was stirred two days at ambient temperature, then was diluted with ether and quenched by slow addition of 3N NaOH. The organic phase was washed with water and saturated NaCl and was dried (anhydrous MgSO4) filtered and evaporated to an oil which was converted to the maleate salt by the addition of ethereal maleic acid (4.2 g, 51%, mp 155°–158° C.). This material was recrystallized twice from isopropanol to yield 2.6 g of 7,8-dimethoxy-1-(4-fluorophenoxy)-2,3,4,5-tetrahydro-3-benzazepine maleate d 168°–169° C.

Calculated for $C_{18}H_{20}FNO_3.C_4H_4O_4$: 60.96%C, 5.58%H, 3.23%N, Found: 60.99%C, 5.58%H, 3.21%N.

EXAMPLE 43

7,8-Dimethoxy-1-(4-fluorophenoxy)-3-methyl-2,3,4,5-tetrahydro-3-benzazepine maleate 7,8-Dimethoxy-1-(4-fluorophenoxy)-2,3,4,5-tetrahydro-3-benzazepine (3.5 g, 11 m mole) of Example 42 was dissolved in 9 ml 95% formic acid and to this was added 8 ml 37% formaldehyde solution. The mixture was stirred at 75° C. for one hour, then was cooled, diluted with water and basified with sodium carbonate. The oil which separated was extracted with ether then was washed with water, dried (saturated NaCl, anhydrous MgSO4), filtered and evaporated to an oil. The oil was converted as in Example 42 to the maleate salt (3.7 g, mp 125°–135° C.). This material was recrystallized twice from isopropanol to yield 2.7 g (55%) of 7,8-dimethoxy-1-(4-fluorophenoxy)-3-methyl-2,3,4,5-tetrahydro-3-benzazepine maleate d 152°–153° C.

Calculated for $C_{19}H_{22}FNO_3.C_4H_4O_4$: 61.73%C, 5.86%H, 3.13%N, Found: 61.69%C, 5.90%H, 3.11%N.

EXAMPLE 44

7,8-Dimethoxy-3-ethyl-1-phenoxy-2,3,4,5-tetrahydro-3-benzazepine maleate

To a solution of 7,8-dimethoxy-1-phenoxy-2,3,4,5-tetrahydro-3-benzazepine (3 g, 10 m mole) and triethylamine (1.2 g, 12 m mole) in 100 ml chloroform was added a solution of acetyl chloride (0.9 g, 12 m mole) in 20 ml chloroform. After one hour, the mixture was evaporated, stirred with water and extracted into ether. The organic extracts were washed with water, saturated NaCl and were dried, filtered and evaporated to 4 g of a viscous oil. A solution of 3-acetyl-7,8-dimethoxy-1-phenoxy-2,3,4,5-tetrahydro-3-benzazepine (3.4 g, 10 mmole) in 125 ml tetrahydrofuran was slowly dropped into a stirring suspension of LiAlH4 (1 g, 26 mmole) in 100 ml THF. After stirring two hours at ambient temperature the reaction mixture was diluted with ether, then quenched by slow addition of saturated ammonium chloride. After filtering, the organic phase was washed with water, saturated NaCl and was dried (anhydrous MgSO4), filtered and evaporated to 3.4 g of an oil. This oil was purified by column chromatography (silica gel, tetrahydrofuran) to give 2 g of an oil. This oil was converted to the maleate salt by the addition of etheral-maleic acid and recrystallized from isopropanol/ether to give 2 g (45%) of 7,8-dimethoxy-3-ethyl-1-phenoxy-2,3,4,5-tetrahydro-3-benzazepine maleate, mp 129°–130° C.

ANALYSIS: Calculated for $C_{20}H_{25}NO_3.C_4H_4O_4$: 64.99%C, 6.59%H, 3.16%N, Found: 65.24%C 6.58%H, 3.05%N.

EXAMPLE 45

1-(4-Chlorophenoxy)-7,8-dimethoxy-2,3,4,5-tetrahydro-3-benzazepine maleate

To a solution of 7,8-dimethoxy-1-hydroxy-2,3,4,5-tetrahydro-3-(p-toluenesulfonyl)-3-benzazepine (20 g, 53 mmole), 4-chlorophenol (6.8 g, 53 mmole) and triphenylphosphine (14.6 g, 56 mmole) in 400 ml benzene, cooled with an ice bath, was slowly dropped a solution of diethyl azodicarboxylate (9.7 g, 56 mmole) in 120 ml benzene. After stirring twenty hours at ambient temperature, the reaction mixture was filtered to remove sym-dicarbethoxyhydrazine (8 g, 86%, m.p. 131°-132°), then evaporated to yield 48 g of an oil which was purified by HPLC (silica gel, dichloromethane) to give 20 g (78%) of an oil. A solution of 1-(4-chlorophenoxy)-7,8-dimethoxy-2,3,4,5-tetrahydro-3-(p-toluenesulfonyl)-3-benzazepine (20 g, 41 mmole) in sodium aluminum bis (2-methoxyethoxy) hydride (3.4 M in toluene, 200 ml, 0.8 mole) was stirred 2.5 days at ambient, temperature, then was diluted with anhydrous ether and was quenched by slow addition of 3N NaOH. The organic phase was washed with water and saturated NaCl and was dried (anhydrous $MgSO_4$), filtered and evaporated to yield 16 g of an oil which was converted to the maleate salt, then immediately was rebasified to give 6.5 g (47%) of an oil. The oil was purified by HPLC (silica gel, 1% diethylamine/ethylacetate) to give 4.4 g of an oil, of which 2.3 g was converted to the maleate salt as in Example 42, then recrystallized from isopropanol/ether to give 2.2 g of 1-(4-chlorophenoxy)-7,8-dimethoxy-2,3,4,5-tetrahydro-3-benzazepine maleate, d 135°-137° C.

ANALYSIS: Calculated for $C_{18}H_{20}ClNO_3 \cdot C_4H_4O_4$: 58.73%C, 5.38%H, 3.11%N, Found: 58.61%C, 5.32%H, 3.02%N.

EXAMPLE 46

1-(4-Chlorophenoxy)-7,8-dimethoxy-3-methyl-2,3,4,5-tetrahydro-3-benzazepine maleate 1-(4-Chlorophenoxy)-7,8-dimethoxy-2,3,4,5-tetrahydro-3-benzazepine (3 g, 6 mmole) was dissolved in 9 ml 95% formic acid and to this was added 8 ml 37% formaldehyde solution. The mixture was stirred at 75° C. for one hour, then was cooled, diluted with water and basified with sodium carbonate. The oil which separated was extracted with ether, washed with water, saturated NaCl, was dried (anhydrous $MgSO_4$), filtered and evaporated to 2.1 g of an oil. This oil was converted to the maleate salt and recrystallized from isopropanol-ether to give 1.9 g (68%) of 1-(4-chlorophenoxy)-7,8-dimethoxy-3-methyl-2,3,4,5-tetrahydro-3-benzazepine maleate, d 153°-154° C.

ANALYSIS: Calculated for $C_{19}H_{22}ClNO_3 \cdot C_4H_4O_4$: 59.54%C, 5.65%H, 3.02%N, Found: 59.93%C, 5.74%H, 2.91%N.

EXAMPLE 47

7,8-Dimethoxy-3-[4,4-bis-(p-fluorophenyl)butyl]-1-phenoxy-2,3,4,5-tetrahydro-3-benzazepine oxalate A mixture of 7,8-dimethoxy-1-phenoxy-2,3,4,5-tetrahydro-3-benzazepine of Example 35 (2.6 g, 8.7 mmole), 4,4-bis-(p-fluorophenyl)-butyl chloride (2.9 g, 10.4 mmole), potassium carbonate (3 g, 22 mmole) and 0.01 g potassium iodide in 90 ml dimethylformamide was stirred twenty hours at 80° C. The reaction mixture was cooled and concentrated to an oil that was stirred with water and extracted with ether. The organic extracts were washed with water and saturated NaCl, and were dried (anhydrous $MgSO_4$), filtered and evaporated to 6 g of an oil. This oil was purified by column chromatography (alumina, ether) to give 5 g of an oil, then by high pressure liquid chromatography (silica gel, 5% ethyl acetate/dichloromethane) to give 2.3 g of a light oil. This oil was converted to the oxalate salt as in Example 1 and recrystallized from isopropanol/ether to give 1.8 g (33%) of 7,8-dimethoxy-3-[4,4-bis-(p-fluorophenyl)butyl]-1-phenoxy-2,3,4,5-tetrahydro-3-benzazepine oxalate, d 114°-116° C.

ANALYSIS: Calculated for $C_{34}H_{35}F_2NO_3 \cdot (CO_2H)_2$: 68.23%C, 5.89%H, 2.21%N, Found: 68.32%C, 5.93%H, 2.24%N.

EXAMPLE 48

1-(4-Bromophenoxy)-7,8-dimethoxy-2,3,4,5-tetrahydro-3-benzazepine maleate

A solution of 7,8-dimethoxy-1-phenoxy-2,3,4,5-tetrahydro-3-benzazepine of Example 35 (6.5 g, 22 mmole) in 300 ml methanol was acidified to pH 1 with ethereal hydrogen chloride. After this solution was cooled with an ice bath, N-bromosuccinimide (4.2 g, 24 mmole) was added. The reaction mixture slowly warmed to ambient temperature, was evaporated, stirred with water, basified with saturated sodium carbonate and was extracted with ethyl acetate-ether. The organic extracts were washed with water, saturated sodium chloride and were dried (anhydrous $MgSO_4$), filtered and evaporated to 8 g of an oil. This oil was converted to the maleate salt (8 g, 74%, m.p. 95°-100° C.) by the addition of ethereal maleic acid of which 4 g was recrystallized twice from isopropanol-ether to give 2.4 g (45%) of 1-(4-bromophenoxy)-7,8-dimethoxy-2,3,4,5-tetrahydro-3-benzazepine maleate, d 145°-146° C.

ANALYSIS: Calculated for $C_{18}H_{20}BrNO_3 \cdot C_4H_4O_4$: 53.45%C, 4.89%H, 2.83%N, Found: 53.78%C, 4.95%H, 2.83%N.

EXAMPLE 49

7,8-Dimethoxy-1-(4-nitrophenoxy)-2,3,4,5-tetrahydro-3-benzazepine maleate

To a suspension of sodium hydride (50% oil dispersion washed with hexanes, 1 g, 21 mmole) in 10 ml dimethylformamide (DMF) was added dropwise a solution of 7,8-dimethoxy-1-hydroxy-2,3,4,5-tetrahydro-3-benzazepine (4 g, 18 mmole) in 30 ml DMF. The mixture was warmed to 65° C. for one hour, then was cooled with an ice bath and a solution of 1-fluoro-4-nitrobenzene (2.7 g, 19 mmole) in 20 ml DMF was slowly added. After slowing warming to ambient temperature the reaction mixture was stirred with 300 ml water and was extracted with ethyl acetate-ether. The organic extract was washed with water and saturated NaCl and was dried (anhydrous $MgSO_4$), filtered and evaporated to 9 g of an oil. This oil was purified by high pressure liquid chromatography (HPLC) [silica gel, 5% methanol/dichloromethane] to give 3.3 g (53%) of a solid. This material was converted to the maleate salt as in Example 48 and was recrystallized twice from isopropanol to give 3 g (36%) of 7,8-dimethoxy-1-(4-nitrophenoxy)-2,3,4,5-tetrahydro-3-benzazepine maleate, d 158°-159° C.

ANALYSIS: Calculated for $C_{18}H_{20}N_2O_5 \cdot C_4H_4O_4$: 57.39%C, 5.25%H, 6.09%N, Found: 57.65%C, 5.40%H, 6.08%N.

EXAMPLE 50

7,8-Dimethoxy-3-(3-phenoxypropyl)-1-phenoxy-2,3,4,5-tetrahydro-3-benzazepine A mixture of 7,8-dimethoxy-1-phenoxy-2,3,4,5-tetrahydro-3-benzazepine of Example 35 (4.8 g, 16 mmole) and 3-phenoxypropyl bromide (4 g, 18 mmole) in 25 ml DMF containing potassium carbonate (milled, 4.4 g, 32 mmole) was stirred at 80° C. for two hours. After cooling, the mixture was stirred with 300 ml water and was extracted with ethyl acetate-ether. The organic extract was washed with water, saturated NaCl and was dried (anhydrous MgSO$_4$), filtered and evaporated to 9 g of an oil. This oil was purified by HPLC (silica gel, 10% ethyl acetate/dichloromethane) to give 4.7 g (68%) of 7,8-dimethoxy-3-(3-phenoxypropyl)-1-phenoxy-2,3,4,5-tetrahydro-3-benzazepine solid, m.p. 95°-100° C.

ANALYSIS: Calculated for $C_{27}H_{31}NO_4$: 74.80%C, 7.21%H, 3.23%N, Found: 74.98%C, 7.23%H, 3.20.

EXAMPLE 51

7,8-Dimethoxy-1-phenoxy-3-(n-propyl)-2,3,4,5-tetrahydro-3-benzazepine oxalate To a solution of 7,8-dimethoxy-1-phenoxy-2,3,4,5-tetrahydro-3-benzazepine of Example 35 (5.8 g, 19 mmole) in 150 ml dichloromethane containing sodium bicarbonate (3.6 g, 43 mmole) was added a solution of propionyl chloride (2 g, 21 mmole) in 25 ml dichloromethane. After stirring one hour at ambient temperature the reaction mixture was evaporated, stirred with water and extracted with ethyl acetate-ether. The organic extract was washed with water, then with dilute HCl, again with water and saturated NaCl and was dried (anhydrous MgSO$_4$), filtered and evaporated to 6.1 g (88%) of an oil. A solution of the resultant 7,8-dimethoxy-1-phenoxy-3-propionyl-2,3,4,5-tetrahydro-3-benzazepine (6 g, 17 mmole) in 100 ml tetrahydrofuran (THF) was slowly added to a solution of lithium aluminum hydride (1M in THF, 1.3 g, 34 mmole, 35 ml), cooled with an ice bath. After stirring two hours at ambient temperature, the reaction mixture was diluted with anhydrous ether and was quenched by slow addition of saturated NH$_4$Cl. The mixture was filtered and the organic layer was washed with water, saturated NaCl and was dried (anhydrous MgSO$_4$), filtered and evaporated to 6 g of an oil. This oil was purified by HPLC (silica gel, 10% ethyl acetate/dichloromethane) to give 3 g (52%) of an oil. This oil was converted to the oxalate salt as in Example 1 and recrystallized from isopropanol-ether to give 3.3 g (45%) of 7,8-dimethoxy-1-phenoxy-3-(n-propyl)-2,3,4,5-tetrahydro-3-benzazepine oxalate, d 113°-115° C.

ANALYSIS: Calculated for $C_{21}H_{27}NO_3.C_2H_2O_4$: 64.02%C, 6.77%H, 3.25%N, Found: 63.95%C, 6.89%H, 3.18%N.

EXAMPLE 52

7,8-Dimethoxy-3-(2-phenethyl)-1-phenoxy-2,3,4,5-tetrahydro-3-benzazepine

A mixture of 7,8-dimethoxy-1-phenoxy-2,3,4,5-tetrahydro-3-benzazepine of Example 35, (3 g, 10 mmole), (2-bromoethyl)benzene (2.0 g, 11 mmole) and potassium carbonate (milled, 3 g, 22 mmole) in 25 ml dimethylformamide was stirred at 70° C. for three hours then was cooled, stirred with 300 ml water and was extracted with ethyl acetate-ether. The organic extract was washed with water, then with saturated NaCl and was dried (anhydrous MgSO$_4$), filtered and evaporated to 5 g of an oil. This oil was purified by HPLC (silica gel, 10% ethyl acetate/dichloromethane) to give 2.5 g (63%) of a solid, m.p. 90°-92° C. This material was recrystallized from isopropyl ether/petroleum ether to give 1.9 g (48%) of 7,8-dimethoxy-3-(2-phenethyl)-1-phenoxy-2,3,4,5-tetrahydro-3-benzazepine, m.p. 93°-94° C.

ANALYSIS: Calculated for $C_{26}H_{29}NO_3$: 77.39%C, 7.24%H, 3.47%N, Found: 77.06%C, 7.31%H, 3.43%N.

EXAMPLE 53

7,8-Dimethoxy-3-ethyl-1-(4-fluorophenoxy)-2,3,4,5-tetrahydro-3-benzazepine oxalate To a solution of 7,8-dimethoxy-1-(4-fluorophenoxy)-2,3,4,5-tetrahydro-3-benzazepine of Example 42, (4.3 g, 13.5 mmole) in 100 ml dichloromethane containing sodium bicarbonate (2.3 g, 27 mmole) was slowly added a solution of acetyl chloride (1.2 g, 15.6 mmole) in 25 ml dichloromethane. After stirring three hours at ambient temperature the reaction mixture was evaporated, stirred with water and extracted with ethyl acetate-ether. The organic extract was washed with diluted HCl, water, saturated NaCl and was dried (anhydrous MgSO$_4$), filtered and evaporated to 4.2 g (89%) of an oil. A solution of the resultant 3-acetyl-7,8-dimethoxy-1-(4-fluorophenoxy)-2,3,4,5-tetrahydro-3-benzazepine (4.2 g, 11.7 mmole) in 50 ml tetrahydrofuran was slowly added to a solution of lithium aluminum hydride (1M in THF, 23 mmole, 23 ml). After stirring one hour at ambient temperature the reaction mixture was diluted with anhydrous ether and quenched by slow addition of saturated ammonium chloride. The organic phase was washed with water and saturated NaCl and was dried (anhydrous MgSO$_4$), filtered and evaporated to 4 g of an oil. This oil was converted to the oxalate salt as in Example 1 and was recrystallized from isopropanol-ether to give 2.5 g (49%) of 7,8-dimethoxy-3-ethyl-1-(4-fluorophenoxy)-2,3,4,5-tetrahydro-3-benzazepine oxalate, d 165°-166° C.

ANALYSIS: Calculated for $C_{20}H_{24}FNO_3.C_2H_2O_4$: 60.68%C, 6.02%H, 3.22%N, Found: 60.42%C, 6.06%H, 3.12%N.

EXAMPLE 54

7,8-Dimethoxy-1-(4-methoxyphenoxy)-2,3,4,5-tetrahydro-3-benzazepine maleate

To a solution of 7,8-dimethoxy-1-hydroxy-2,3,4,5-tetrahydro-3-(p-toluenesulfonyl)-3-benzazepine (20 g, 53 mmole), p-methoxyphenol (6.6 g, 53 mmole) and triphenylphosphine (14.6 g, 56 mmole) in 200 ml benzene, cooled with an ice bath, was added over one hour a solution of diethyl azodicarboxylate (9.7 g, 56 mmole) in 100 ml benzene. After stirring twenty hours at ambient temperature, the reaction mixture was filtered to remove sym-dicarbethoxyhydrazine (8.2 g) then evaporated to 50 g of an oil. This oil was purified by HPLC (silica, dichloromethane) to give 17 g (66%) of an oil. A mixture of the resultant 7,8-dimethoxy-1-(4-methoxyphenoxy)-2,3,4,5-tetrahydro-3-(p-toluenesulfonyl)-3-benzazepine (17 g, 35 mmole) and sodium bis(2-methoxyethoxy)aluminum hydride (3.4M in toluene, 0.5 mole, 70 ml) stirred 4 days at ambient temperature then was diluted with anhydrous ether and was quenched by slow addition of 2N NaOH. The phases were separated and the aqueous phase was extracted with dichloromethane. The combined organic phase was dried (anhydrous MgSO$_4$), filtered and evaporated to 13 g of an oil. This oil was converted to the oxalate salt, as in Example 1, then collected and rebasified with sodium carbonate to give 8 g (69%) of an oil. This oil was purified by HPLC (silica, 7% methanol in dichloromethane) to give 5 g (32%) of an oil. This oil was converted to the maleate salt as in Example 48 and recrystallized twice from isopropanol-ether to give 5 g (32%) of 7,8-dimethoxy-1-(4-methoxyphenoxy)-2,3,4,5-tetrahydro-3-benzazepine maleate, d 171°–172° C.

ANALYSIS: Calculated for C$_{19}$H$_{23}$NO$_4$.C$_4$H$_4$O$_4$: 62.01%C, 6.11%H, 3.15%N, Found: 61.70%C, 6.07%H, 3.05%N.

EXAMPLE 55

1-(2-Chlorophenoxy)-7,8-dimethoxy-2,3,4,5-tetrahydro-3-benzazepine maleate

A solution of 7,8-dimethoxy-1-hydroxy-2,3,4,5-tetrahydro-3-benzazepine (5.4 g, 0.024 mol) in hexamethylphosphoramide (HMPA) (50 ml) was added dropwise under nitrogen to a suspension of sodium hydride (1 g, 60% NaH oil dispersion, 5% excess, 0.025 mol, washed twice with hexane) in HMPA (10 ml). After addition was complete, the reaction mixture was warmed to 65° C., and this solution of the alkoxide in HMPA was then added dropwise under nitrogen to a solution of o-dichlorobenzene (3.9 g, 0.026 10% excess) in HMPA (25 ml) at 80° C. After addition was complete, the reaction mixture was heated at 80° C. for an additional hour. The mixture was poured over ice and extracted several times with dichloromethane. The dichloromethane extract was washed thrice with water, then with saturated sodium chloride solution, then dried over magnesium sulfate. Removal of the dichloromethane under vacuum gave 11.4 g of an oil which was HPLC chromatographed using 5% CH$_3$OH/CH$_2$Cl$_2$ with a single gel column. The resultant oil was dissolved in ether and a solution of maleic acid in ether added to form the maleate salt as an oil. The supernatant was decanted and on standing gave a small amount of oil. The first oil was dissolved in warm acetone, ether added, and on standing gave a precipitate (2.2 g, m.p. 155°–156° C). The second oil when treated likewise gave an additional 0.2 g, total 2.4 g (22%) of 1-(2-chlorophenoxy)-7,8-dimethoxy-2,3,4,5-tetrahydro-3-benzazepine maleate.

ANALYSIS: Calculated for C$_{18}$H$_{20}$ClNO$_3$.C$_4$H$_4$O$_4$: 58.72%C, 5.38%H, 3.11%N, Found: 58.44%C, 5.58%H, 3.04%N.

EXAMPLE 56

7,8-Dimethoxy-1-(4-methylphenoxy)-2,3,4,5-tetrahydro-3-benzazepine maleate

To a solution of 7,8-dimethoxy-1-hydroxy-2,3,4,5-tetrahydro-3-(p-toluenesulfonyl)-3-benzazepine (31 g, 82 mmole), p-cresol (8.9 g, 82 mmole) in 400 ml benzene, cooled with an ice bath, was added over one hour, a solution of diethyl azodicarboxylate (15 g, 86 mmoles) in 100 ml benzene. After stirring twenty hours at ambient temperature, the reaction mixture was filtered to remove sym-dicarbethoxyhydrazine (13 g, m.p. 131°–132° C), then evaporated to 69 g of an oil. This oil was purified by HPLC (silica gel, dichloromethane) to give 24 g (63%) of an oil. A solution of the resultant 7,8-dimethoxy-1-(4-methylphenoxy)-2,3,4,5-tetrahydro-3-(p-toluenesulfonyl)-3-benzazepine (24 g, 51 mmole) in 50 ml toluene and sodium bis(2-methoxyethoxy)aluminium hydride (3.4M in toluene, 150 ml, 1 mole hydride) was stirred four days at ambient temperature then was diluted with toluene and quenched by slow addition of dilute NaOH. The mixture was filtered and the organic phase was dried (anhydrous MgSO$_4$), filtered and evaporated to give 16 g of an oil. This oil was converted to the oxalate salt in ether, as in Example 1, then was collected and rebasified with sodium carbonate to give 8.4 g of an oil. This oil was purified by HPLC (silica gel, 5% methanol in dichloromethane to give 6 g (38%) of an oil. 3 g of this oil was converted to the maleate salt as in Example 48 and was recrystallized from isopropanol-ether to give 3.2 g of 7,8-dimethoxy-1-(4-methylphenoxy)-2,3,4,5-tetrahydro-3-benzazepine maleate, m.p. 158°–159° C.

ANALYSIS: Calculated for C$_{19}$H$_{23}$NO$_3$.C$_4$H$_4$O$_4$: 64.32%C, 6.34%H, 3.26%N, Found: 64.17%C, 6.09%H, 3.28%N.

EXAMPLE 57

1-(3,4-Dichlorophenoxy)-7,8-dimethoxy-2,3,4,5-tetrahydro-3-benzazepine oxalate

A solution of 7,8-dimethoxy-1-hydroxy-2,3,4,5-tetrahydro-3-benzazepine (3 g, 13.4 mmole) in 25 ml dimethylformamide was slowly dropped into a stirring suspension of sodium hydride (50% oil dispersion, 0.7 g, 14.8 mmole), previously washed with hexane, in 10 ml dimethylformamide. After the addition was completed, the mixture was warmed for one hour at 60° C., then was cooled and a solution of 3,4-dichlorofluorobenzene (2.4 g, 14.8 mmole) in 10 ml dimethylformamide was added. After stirring two hours at ambient temperature, the reaction mixture was stirred with 400 ml water and was extracted with ethyl acetate. The organic extract was washed with ethyl acetate. The organic extract was washed with water and saturated NaCl and was dried (anhydrous MgSO$_4$), filtered and evaporated to 7 g of an oil. This oil was purified by HPLC (silica gel, 5% methanol in dichloromethane) to give 2.8 g (57%) of an oil. This oil was converted to the oxalate salt as in Example 1 and was recrystallized from ethyl acetate-methanol to give 2.1 g (34%) of 1,(3-4-dichlorophenoxy)-7,8-dimethoxy-2,3,4,5-tetrahydro-3-benzazepine oxalate, d 167°–168° C.

ANALYSIS: Calculated for C$_{18}$H$_{19}$Cl$_2$NO$_3$.C$_2$H$_2$O$_4$: 52.41%C, 4.62%H, 3.06%N, Found: 52.18%C, 4.53%H, 3.00%N.

EXAMPLE 58

7,8-Dimethoxy-1-(3-fluorophenoxy)-2,3,4,5-tetrahydro-3-benzazepine maleate

A solution of 7,8-dimethoxy-1-hydroxy-2,3,4,5-tetrahydro-3-benzazepine (6.8 g, 30.4 mmole) in 60 ml dimethylformamide was slowly added to a suspension of sodium hydride (50% oil dispersion, 1.7 g 35 mmole), previously washed with hexane, in 10 ml dimethylformamide. The reaction mixture stirred at 60° C. for one hour, then a solution of m-difluorobenzene (4.2 g, 37 mmole) in 20 ml dimethylformamide was added. After stirring at 60° C. for one hour, the reaction mixture was cooled, stirred with water and extracted with ethyl acetate-ether. The organic extract was washed with water and saturated NaCl and was dried (anhydrous MgSO$_4$), filtered and evaporated to 9.5 g of an oil. This oil was purified by HPLC (silica gel, 5% methanol in dichloromethane) to give 3.9 g (40%) of an oil. This oil was converted to the maleate salt as in Example 48 and then recrystallized twice from isopropanol-ether to give 3.5 g (27%) of 7,8-dimethoxy-1-(3-fluorophenoxy)-2,3,4,5-tetrahydro-3-benzazepine maleate, m.p. 157°–158° C.

ANALYSIS: Calculated for $C_{18}H_{20}FNO_3 \cdot C_4H_4O_4$: 60.96%C, 5.58%H, 3.23%N, Found: 60.66%C, 5.62%H, 3.19%N.

EXAMPLE 59

1-(3-Chlorophenoxy)-7,8-dimethoxy-3-methyl-2,3,4,5-tetrahydro-3-benzazepine maleate A solution of 1-(3-chlorophenoxy)-7,8-dimethoxy-2,3,4,5-tetrahydro-3-benzazepine of Example 22 (5 g, 15 mmole) in 18 ml 95% formic acid and 6 ml of 37% aqueous formaldehyde was stirred for one hour at 75° C. then was cooled, diluted with water, basified with sodium carbonate and extracted with ether. The organic extract was washed with water and saturated sodium chloride and was dried (anhydrous MgSO₄), filtered and evaporated to 5 g of an oil. This oil was purified by HPLC (silica gel, ethyl acetate) to give 3.1 g (60%) of an oil. This oil was converted to the maleate salt as in Example 48 and was thrice recrystallized from isopropanol-ether to give 2.5 g (36%) of 1-(3-chlorophenoxy)-7,8-dimethoxy-3-methyl-2,3,4,5-tetrahydro-3-benzazepine maleate, m.p. 146°–148° C.

ANALYSIS: Calculated for $C_{19}H_{22}ClNO_3 \cdot C_4H_4O_4$: 59.55%C, 5.65%H, 3.02%N, Found: 59.36%C, 5.62%H, 2.99%N.

EXAMPLE 60

7,8-Dimethoxy-3-methyl-1-(4-methylphenoxy)-2,3,4,5-tetrahydro-3-benzazepine maleate A solution of 7,8-dimethoxy-1-(4-methylphenoxy)-2,3,4,5-tetrahydro-3-benzazepine of Example 56 (3 g, 9.6 mmole) in 10 ml 95% formic acid and 9 ml 37% aqueous formaldehyde stirred for two hours at 70° C. then was cooled, diluted with water, basified with sodium carbonate and extracted with ethyl acetate-ether. The organic extract was washed with water and saturated sodium chloride and was dried (anhydrous MgSO₄), filtered and evaporated to 3.4 g of an oil. This oil was purified by HPLC (silica gel, ethyl acetate) to give 2.2 g (71%) of an oil. This oil was converted to the maleate salt as in Example 18 and was recrystallized from isopropanol-ether to give 2.7 g (63%) of 7,8-dimethoxy-3-methyl-1-(4-methylphenoxy)-2,3,4,5-tetrahydro-3-benzazepine maleate, m.p. 159°–160° C.

ANALYSIS: Calculated for $C_{20}H_{25}NO_3 \cdot C_4H_4O_4$: 64.99%C, 6.59%H, 3.16%N, Found: 64.87%C, 6.52%H, 3.13%N.

EXAMPLE 61

1-(3,4-Dichlorophenoxy)-7,8-dimethoxy-3-methyl-2,3,4,5-tetrahydro-3-benzazepine maleate A mixture of 1-(3,4-dichlorophenoxy)-7,8-dimethoxy-2,3,4,5-tetrahydro-3-benzazepine of Example 57 (4.7 g, 13 mmole), 15 ml 95% formic acid and 14 ml 37% aqueous formaldehyde was stirred at 70° C. for two hours then was cooled, diluted with 200 ml water and basified with sodium carbonate. The oil that separated was extracted with ethyl acetate-ether and was washed with water, saturated NaCl and was dried (anhydrous MgSO₄), filtered and evaporated to 5 g of an oil. This oil was purified by HPLC (silica gel, ethyl acetate) to give 4 g (82%) of an oil. This oil was converted to the maleate salt as in Example 48 and was recrystallized twice from isopropanol-ether to give 3.6 g (56%) of 1-(3,4-dichlorophenoxy)-7,8-dimethoxy-3-methyl-2,3,4,5-tetrahydro-3-benzazepine maleate, m.p. 143°–144° C.

ANALYSIS: Calculated for $C_{19}H_{21}Cl_2NO_3 \cdot C_4H_4O_4$: 55.43%C, 5.06%H, 2.81%N, Found: 55.19%C, 4.89%H, 2.69%N.

EXAMPLE 62 a.

1-(4-Cyanophenoxy)-7,8-dimethoxy-2,3,4,5-tetrahydro-3-benzazepine

To a suspension of NaH (1 g, 20.6 mmole, 50% oil dispersion), washed with hexanes in 10 ml dimethylformamide (DMF) was slowly added a solution of 7,8-dimethoxy-1-hydroxy-2,3,4,5-tetrahydro-3-benzazepine (4 g, 17.9 mmole) in 30 ml DMF. The mixture was warmed to 65° C. for 1 hour, then cooled to 25° C. A solution of 4-fluorobenzonitrile in 20 ml DMF (2.5 g, 20.6 mmole) was added, dropwise in 20 minutes. The mixture was poured into 300 ml ice water, stirred and extracted with ethyl acetate-ether. The organic extract was washed with water, saturated NaCl and was dried (anhydrous MgSO₄), filtered and evaporated to 7 g of an oil. This oil was purified by high pressure liquid chromatography (HPLC), (silica, 5% methanol/dichloromethane) to give 3.6 g (62%) of an oil which solidified on standing. This material was dissolved in ether, filtered, then converted to the maleate salt as in Example 48. This material was immediately recrystallized twice from isopropanol-ether to give 3.2 g of solid, m.p. d118°–120° C.

Basification of salt and filtrates gave 3 g of an oil of 1-(Cyanophenoxy)-7,8-dimethoxy-2,3,4,5-tetrahydro-3-benzazepine.

b.

1-(4-Cyanophenoxy)-7,8-dimethoxy-3-methyl-2,3,4,5-tetrahydro-3-benzazepine maleate A mixture of 1-(4-cyanophenoxy)-7,8-dimethoxy-2,3,4,5-tetrahydro-3-benzazepine of Example 62(a) (3 g, 9.2 mmole) in 10 ml 95% formic acid and 9 ml 37% aqueous formaldehyde was stirred for two hours at 75° C., then was cooled, stirred with 300 ml water and basified with sodium carbonate. The oil which separated was extracted with ethyl acetate and was washed with water and saturated sodium chloride and was dried (anhydrous MgSO₄), filtered and evaporated to 3.3 g of an oil. This oil was purified by HPLC (silica gel, ethyl acetate) to give 2.5 g (81%) of an oil. This material was converted to the maleate salt (as in Example 48) and was recrystallized twice from isopropanol-ether to give 2.3 g (55%) of 1-(4-cyanophenoxy)-7,8-dimethoxy-3-methyl-2,3,4,5-tetrahydro-3-benzazepine maleate, d 166°–167° C.

ANALYSIS: Calculated for $C_{20}H_{22}N_2O_3 \cdot C_4H_4O_4$: 63.42%C, 5.77%H, 6.17%N, Found: 63.25%C, 5.80%H, 6.19%N.

EXAMPLE 63

7,8-Dimethoxy-2,3,4,5,-tetrahydro-1-(3-trifluoromethylphenoxy)-3-benzazepine maleate A solution of 7,8-dimethoxy-1-hydroxy-2,3,4,5-tetrahydro-3-benzazepine (8 g, 36 mmole) in 60 ml dimethylformamide was slowly added to a suspension of sodium hydride (50% oil dispersion, 2.0 g, 41 mmole), previously washed with hexanes, in 10 ml dimethylformamide. After the addition was completed, the reaction mixture stirred for one hour at 60° C., then was cooled, and a solution of m-fluorobenzotrifluoride (7.1 g, 43 mmole) in 20 ml dimethylformamide was added. After stirring twenty hours at ambient temperature, the reaction mixture was stirred with 500 ml water and was extracted with dichloromethane. The organic extract was washed with water and saturated sodium chloride and was dried (anhydrous MgSO4), filtered and evaporated to 13 g of an oil. This oil was purified by HPLC (silica gel, 5% methanol in dichloromethane) to give 5.3 g (40%) of an oil. This oil was converted to the maleate salt as in Example 48 and was recrystallized twice from isopropanol-ether to give 3.4 g (20%) of 7,8-dimethoxy-2,3,4,5-tetrahydro-1-(3-trifluoromethylphenoxy)-3-benzazepine maleate, d 168°–169° C.

ANALYSIS:

Calculated for $C_{19}H_{20}F_3NO_3.C_4H_4O_4$: 57.14%C, 5.00%H, 2.90%N, Found: 57.23%C, 5.01%H, 1.86%N.

EXAMPLE 64

7,8-Dimethoxy-3-methyl-2,3,4,5-tetrahydro-1-(3-trifluoromethylphenoxy)-3-benzazepine hydrochloride A solution of 7,8-dimethoxy-2,3,4,5-tetrahydro-1-(3-trifluoromethylphenoxy)-3-benzazepine of Example 63, (3 g, 8.2 mmole) in 10 ml 95% formic acid and 10 ml 37% aqueous formaldehyde was stirred for two-hours at 80° C., then was cooled, stirred with water, basified with sodium carbonate and was extracted with ethyl acetate. The organic extract was washed with water and saturated sodium chloride and was dried (anhydrous MgSO4), filtered and evaporated to 3 g of an oil. This oil was purified by HPLC (silica gel, ethyl acetate) to give 2.5 g (81%) of an oil. This oil was converted to the hydrochloride salt and was recrystallized from isopropanol-methanol to give 2.2 g (64%) of 7,8-dimethoxy-3-methyl-2,3,4-5-tetrahydro-1-(3-trifluoromethylphenoxy)-3-benzazepine hydrochloride, d 216°–217° C.

ANALYSIS: Calculated for $C_{20}H_{22}F_3NO_3.HCl$: 57.49%C, 5.55%H, 3.35%N, Found: 57.43%C, 5.73%H, 3.28%N.

EXAMPLE 65

3-[2-(4-Aminophenyl)ethyl]-7,8-dimethoxy-1-phenoxy-2,3,4,5-tetrahydro-3-benzazepine dioxalate A mixture of 7,8-dimethoxy-1-phenoxy-2,3,4,5-tetrahydro-3-benzazepine of Example 35, (5.7 g, 19 mmole), p-nitrophenethyl bromide (5.5 g, 24 mmole), potassium carbonate (milled, 7.9 g, 57 mmole) and 0.1 g potassium iodide in 50 ml dimethylformamide was stirred at 80° C. for three hours then at ambient temperature for 20 hours. The reaction mixture was stirred with 500 ml water and was extracted with ethyl acetate-ether. The organic extract was washed with water and saturated sodium chloride and was dried (anhydrous MgSO4), filtered and evaporated to 10 g of an oil. This oil was purified by HPLC (silica gel, 5% ethyl acetate in dichloromethane) to give 5 g (59%) of an oil. A solution of the resulting 7,8-dimethoxy-3-[2-(4-nitrophenyl)ethyl]-1-phenoxy-2,3,4,5-tetrahydro-3-benzazepine (5 g, 11 mmole) in 30 ml glacial acetic acid was slowly added to a stirring suspension of zinc dust (3.5 g, 49 mmole) in 60 ml 50% aqueous acetic acid. After stirring one hour at ambient temperature the reaction mixture was filtered, basified with sodium carbonate and extracted with ethyl acetate-ether. The organic extract was washed with water and saturated sodium chloride and was dried (anhydrous MgSO4), filtered and evaporated to 4.8 g of an oil. The oil was purified by HPLC (50% ethyl acetate/dichloromethane) to give 2.8 g (35% overall) of an oil. This oil was converted to the dioxalate salt utilizing the procedure of Example 1 and was recrystallized twice from ethyl acetate to give 2.2 g (19%) of 3-[2-(4-aminophenyl)ethyl]-7,8-dimethoxy-1-phenoxy-2,3,4,5-tetrahydro-3-benzazepine dioxalate, m.p. 125°–126° C.

ANALYSIS: Calculated for $C_{26}H_{30}N_2O_3.2(CO_2H)_2$: 60.19%C, 5.73%H, 4.68%N, Found: 60.09%C, 5.73%H, 4.62%N.

EXAMPLE 66

7,8-Dimethoxy-3-methyl-1-(4-nitrophenoxy)-2,3,4,5-tetrahydro-3-benzazepine oxalate A solution of 7,8-dimethoxy-1-(4-nitrophenoxy)-2,3,4,5-tetrahydro-3-benzazepine of Example 49, (6 g, 17.4 mmole) in 25 ml 95% formic acid and 25 ml 37% aqueous formaldehyde solution was stirred at 75° C. for 1.5 hours. After cooling, the reaction mixture was stirred with water, basified with sodium carbonate and was extracted with dichloromethane. The organic extract was washed with water and saturated sodium chloride and was dried (anhydrous MgSO4), filtered and evaporated to 6.2 g of an oil. This oil was purified by high pressure liquid chromatography (silica gel, ethyl acetate) to give 4.6 g (74%) of an oil. This oil was converted to the oxalate salt as in Example 1 and was twice recrystallized from isopropanol-methanol to give 3.4 g (44%) of 7,8-dimethoxy-3-methyl-1-(4-nitrophenoxy)-2,2,4,5-tetrahydro-3-benzazepine oxalate, d 158°–159° C.

ANALYSIS: Calculated for $C_{19}H_{22}N_2O_5.(CO_2H)_2$: 56.24%C, 5.39%H, 6.25%N, Found: 56.39%C, 5.54%H, 6.34%N.

EXAMPLE 67

1-(3-Chlorophenoxy)-7,8-dimethoxy-3-(n-propyl)-2,3,4,5-tetrahydro-3-benzazepine hydrochloride To a solution of 1-(3-chlorophenoxy)-7,8-dimethoxy-2,3,4,5-tetrahydro-3-benzazepine of Example 22, 6 g, 18 mmole) in 200 ml dichloromethane containing sodium bicarbonate (5 g, 60 mmole) was added a solution of propionyl chloride (1.9 g, 21 mmole) in 25 ml dichloromethane. After stirring 20 hours at ambient temperature, the reaction mixture was evaporated, stirred with water and extracted with ethyl acetate. The organic extract was washed with water, dilute HCl, again with water and saturated sodium chloride and was dried (anhydrous MgSO4), filtered and evaporated to 5 g (74%) of an oil. This oil was purified by high pressure liquid chromatography (HPLC) [silica gel, 10% ethyl acetate in dichloromethane] to give 4.6 g (66%) of an oil. A solution of the resultant 1-(3-chlorophenoxy)-7,8-dimethoxy-3-propionyl)-2,3,4,5-tetrahydro-3-benzazepine (12 mmole) in 25 ml tetrahydrofuran was slowly added to a solution of borane in tetrahydrofuran (1.04M, 50 ml, 50 mmole), cooled with an ice bath. After warming to ambient temperature the mixture was stirred for two hours, then was slowly acidified with 3N HCl and stirred at 85° C. for two hours. After cooling, the mixture was stirred with water, basified with sodium carbonate and extracted with dichloromethane. The organic extract was washed with water and saturated sodium chloride and was dried (anhydrous MgSO₄), filtered and evaporated to 4.6 g of an oil. This oil was purified by HPLC (silica gel, 20% ethyl acetate in dichloromethane) to give 2.0 g (48%) of an oil. This oil was converted to the hydrochloride salt as in Example 3 and was recrystallized from isopropanol-ether to give 1.6 g (22%) of 1-(3-chlorophenoxy)-7,8-dimethoxy-3-(n-propyl)-2,3,4,5-tetrahydro-3-benzazepine hydrochloride, d 143°-144° C.

ANALYSIS: Calculated for $C_{21}H_{26}ClNO_3 \cdot HCl$: 61.17%C, 6.60%H, 3.40%N, Found: 61.51%C, 6.54%H, 3.43%N.

We claim:

1. A compound having the formula

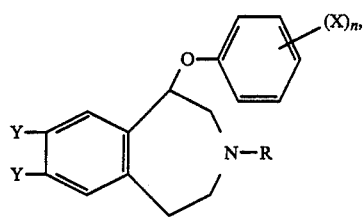

wherein Y is the same or different and is hydrogen and lower alkoxy; X is hydrogen, halogen, lower alkyl, lower alkoxy, $CF_3$, $NO_2$ and $NH_2$: R is hydrogen, lower alkyl, cycloalkyl lower alkyl,

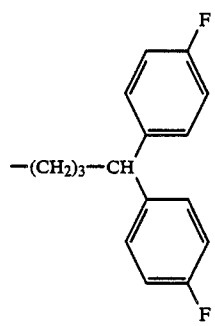

Ar lower alkyl of the formula

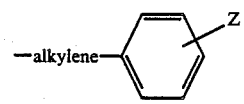

where Z is hydrogen, lower alkyl, lower alkoxy, $CF_3$, $NO_2$ and $NH_2$; Aryloxy lower alkyl of the formula

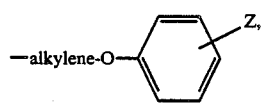

where Z is as defined; and an alkylene amine of the formula

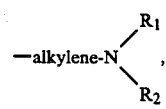

where $R_1$ and $R_2$ are the same or different and are hydrogen and lower alkyl; n is an integer of 1 or 2; and the acceptable acid addition salts thereof.

2. The compound as defined in claim 1 wherein R is hydrogen.

3. The compound as defined in claim 1 wherein R is lower alkyl.

4. The compound as defined in claim 1 which is 7,8-dimethoxy-1-(4-nitrophenoxy)-2,3,4,5-tetrahydro-3-benzazepine or a pharmaceutically acceptable salt thereof.

5. The compound as defined in claim 1 which is 7,8-dimethoxy-3-(3-phenoxypropyl)-1-phenoxy-2,3,4,5-tetrahydro-3-benzazepine or a pharmaceutically acceptable salt thereof.

6. The compound as defined in claim 1 which is 7,8-dimethoxy-1-phenoxy-3-(n-propyl)-2,3,4,5-tetrahydro-3-benzazepine or a pharmaceutically acceptable salt thereof.

7. The compound as defined in claim 1 which is 7,8-dimethoxy-3-(2-phenethyl)-1-phenoxy-2,3,4,5-tetrahydro-3-benzazepine or a pharmaceutically acceptable salt thereof.

8. The compound as defined in claim 1 which is 7,8-dimethoxy-3-ethyl-1-(4-fluorophenoxy)-2,3,4,5-tetrahydro-3-benzazepine or a pharmaceutically acceptable salt thereof.

9. The compound as defined in claim 1 which is 7,8-dimethoxy-1-(4-methoxyphenoxy)-2,3,4,5,-tetrahydro-3-benzazepine or a pharmaceutically acceptable salt thereof.

10. The compound as defined in claim 1 which is 1-(2-chlorophenoxy)-7,8-dimethoxy-2,3,4,5-tetrahydro-3-benzazepine or a pharmaceutically acceptable salt thereof.

11. The compound as defined in claim 1 which is 7,8-dimethoxy-1-(4-methylphenoxy)-2,3,4,5-tetrahydro-3-benzazepine or a pharmaceutically acceptable salt thereof.

12. The compound as defined in claim 1 which is 1-(3,4-dichlorophenoxy)-7,8-dimethoxy-2,3,4,5-tetrahydro-3-benzazepine or a pharmaceutically acceptable salt thereof.

13. The compound as defined in claim 1 which is 7,8-dimethoxy-1-(3-fluorophenoxy)-2,3,4,5-tetrahydro-3-benzazepine or a pharmaceutically acceptable salt thereof.

14. The compound as defined in claim 1 which is 1-(3-chlorophenoxy)-7,8-dimethoxy-3-methyl-2,3,4,5-tetrahydro-3-benzazepine or a pharmaceutically acceptable salt thereof.

15. The compound as defined in claim 1 which is 7,8-dimethoxy-3-methyl-1-(4-methylphenoxy)-2,3,4,5-tetrahydro-3-benzazepine or a pharmaceutically acceptable salt thereof.

16. The compound as defined in claim 1 which is 1-(3,4,-dichlorophenoxy)-7,8-dimethoxy-3-methyl-2,3,4,5-tetrahydro-3-benzazepine or a pharmaceutically acceptable salt thereof.

17. The compound as defined in claim 1 which is 1-(4-cyanophenoxy)-7,8-dimethoxy-3-methyl-2,3,4,5-tetrahydro-3-benzazepine or a pharmaceutically acceptable salt thereof.

18. The compound as defined in claim 1 which is 7,8-dimethoxy-2,3,4,5-tetrahydro-1-(3-trifluoromethylphenoxy)-3-benzazepine or a pharmaceutically acceptable salt thereof.

19. The compound as defined in claim 1 which is 7,8-dimethoxy-b 3-methyl-2,3,4,5-tetrahydro-1-(3-trifluoromethylphenoxy)-3-benzazepine or a pharmaceutically acceptable salt thereof.

20. The compound as defined in claim 1 which is 3-[2-(4-aminophenyl)ethyl]-7,8-dimethoxy-1-phenoxy-2,3,4,5-tetrahydro-3-benzazepine or a pharmaceutically acceptable salt thereof.

21. The compound as defined in claim 1 which is 7,8-dimethoxy-3-methyl-1-(4-nitrophenoxy)-2,3,4,5-tetrahydro-3-benzazepine or a pharmaceutically acceptable salt thereof.

22. The compound as defined in claim 1 which is 1-(3-chlorophenoxy)-7,8-dimethoxy-3-(n-propyl)-2,3,4,5-tetrahydro-3-benzazepine or a pharmaceutically acceptable salt thereof.

* * * * *